United States Patent
Sahay et al.

(10) Patent No.: US 10,287,580 B2
(45) Date of Patent: May 14, 2019

(54) MOLECULAR RE-ENGINEERING OF EXCITATION-INHIBITION BALANCE IN MEMORY CIRCUITS

(71) Applicant: The General Hospital Corporation, Boston, MA (US)

(72) Inventors: Amar Sahay, Lexington, MA (US); Nannan Guo, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/125,796

(22) PCT Filed: Mar. 13, 2015

(86) PCT No.: PCT/US2015/020540
§ 371 (c)(1),
(2) Date: Sep. 13, 2016

(87) PCT Pub. No.: WO2015/138960
PCT Pub. Date: Sep. 17, 2015

(65) Prior Publication Data
US 2016/0376588 A1  Dec. 29, 2016

Related U.S. Application Data

(60) Provisional application No. 61/952,934, filed on Mar. 14, 2014.

(51) Int. Cl.
*C12N 15/113* (2010.01)
*A61K 49/00* (2006.01)
*C12Q 1/6897* (2018.01)

(52) U.S. Cl.
CPC ........ *C12N 15/113* (2013.01); *A61K 49/0008* (2013.01); *C12Q 1/6897* (2013.01); *C12N 2310/11* (2013.01); *C12N 2310/12* (2013.01); *C12N 2310/14* (2013.01); *C12N 2310/321* (2013.01); *C12N 2310/322* (2013.01); *C12N 2310/3231* (2013.01); *C12N 2310/3233* (2013.01); *C12N 2310/3521* (2013.01); *C12N 2310/3525* (2013.01); *C12N 2310/3533* (2013.01); *C12N 2310/531* (2013.01)

(58) Field of Classification Search
None
See application file for complete search history.

(56) References Cited

U.S. PATENT DOCUMENTS

2009/0012021 A1\* 1/2009 Sood ................. A61K 48/0025 514/44 R
2011/0023143 A1  1/2011 Weinstein et al.

FOREIGN PATENT DOCUMENTS

WO  WO-2011127222 A1 \* 10/2011 .......... A61K 31/713
WO  2013/185108  12/2013

OTHER PUBLICATIONS

Brummelkamp, et al. (2002) "A System for Stable Expression of Short Interfering RNAs in Mammalian Cells." Science, v.296(5567):550-3. (Year: 2002).\*
Acsady and Kali, "Models, structure, function: the transformation of cortical signals in the dentate gyrus," Prog Brain Res, 2007, 163: 577-599.
Acsady et al., "GABAergic cells are the major postsynaptic targets of mossy fibers in the rat hippocampus," J Neurosci, 1998, 18:3386-3403.
Bakker et al., "Pattern separation in the human hippocampal CA3 and dentate gyrus," Science, Mar. 2008, 319: 1640-1642.
Bakker et al., "Reduction of hippocampal hyperactivity improves cognition in amnestic mild cognitive impairment," Neuron, May 2012, 74:467-474.
Biedenkapp and Rudy, "Context preexposure prevents forgetting of a contextual fear memory: implication for regional changes in brain activation patterns associated with recent and remote memory tests," Learning & Memory, 2007,14:200-203.
Bragin et al., "Dentate EEG spikes and associated interneuronal population bursts in the hippocampal hilar region of the rat," J of Neurophysiol, Apr. 1995, 73: 1691-1705.
Cao et al., "miR-129-3p controls cilia assembly by regulating CP110 and actin dynamics," Nature Cell Biology, Jun. 2012, 14:697-706.
Clelland et al., "A functional role for adult hippocampal neurogenesis in spatial pattern separation," Science, Jul. 2009, 325:210-213.
Creer et al., "Running enhances spatial pattern separation in mice," PNAS, 2010, 107:2367-2372.
Decker, "The effects of aging on hippocampal and cortical projections of the forebrain cholinergic system," Brain Res, Nov. 1987, 434:423-438.
Deng et al., "Selection of distinct populations of dentate granule cells in response to inputs as a mechanism for pattern separation in mice," eLife, 2013, 2:e00312.
Enkel et al., "Ambiguous-cue interpretation is biased under stress- and depression-like states in rats," Neuropsychopharmacology, 2010, 35: 1008-1015.
Ferrante et al., "Feed-forward inhibition as a buffer of the neuronal input-output relation." PNAS, 2009, 106: 18004-18009.
Ge et al., "A critical period for enhanced synaptic plasticity in newly generated neurons of the adult brain," Neuron, May 2007, 54:559-566.
Geinisman et al., "Age-related loss of axospinous synapses formed by two afferent systems in the rat dentate gyms as revealed by the unbiased stereological dissector technique," Hippocampus, Oct. 1992, 2:437-444.

(Continued)

*Primary Examiner* — Jennifer Pitrak McDonald
(74) *Attorney, Agent, or Firm* — Fish & Richardson P.C.

(57) ABSTRACT

Disclosed are memory-regulating agents and methods that target actin binding LIM protein family, member 3 (ABLIM3). Specifically, the disclosure provides methods of inhibiting Ablim3 using inhibitory nucleic acids that target the Ablim3 gene or mRNA to improve memory in subjects with memory dysfunction associated with Alzheimer's Disease (AD), normal aging, or posttraumatic stress disorder (PTSD). Further disclosed is a cell-based assay that can be used to screen for small molecule regulators of Ablim3 function.

15 Claims, 17 Drawing Sheets

Specification includes a Sequence Listing.

(56) References Cited

OTHER PUBLICATIONS

Gilbert et al, "Dissociating hippocampal subregions: a double dissociation between dentate gyrus and CA1" Hippocampus, 2001, 11:626-636.
Grillon et al., "Increased anxiety during anticipation of unpredictable aversive stimuli in posttraumatic stress disorder but not in generalized anxiety disorder," Biol Psychiatry, 2009, 66:47-53.
Hasselmo et al., Dynamics of learning and recall at excitatory recurrent synapses and cholinergic modulation in rat hippocampal region CA3, 1995, J Neurosci 15:5249-5262.
Hof and Morrison, (2004) The aging brain: morphomolecular senescence of cortical circuits, Trends Neurosci, Oct. 2004, 27:607-613.
Ikrar et al., "Adult neurogenesis modifies excitability of the dentate gyrus," Front Neural Circuits, 2013, 7: 204.
International Preliminary Report on Patentability in International Application No. PCT/US2015/020540, dated Sep. 14, 2016, 8 pages.
Kim et al., "Functional genomic screen for modulators of ciliogenesis and cilium length," Nature, 2010, 464:1048-1051.
Kubik et al., "Using immediate-early genes to map hippocampal subregional functions," Learning & Memory, 2007. 14:758-770.
Kuhn et al., "Neurogenesis in the dentate gyrus of the adult rat: age-related decrease of neuronal progenitor proliferation," J Neurosci, Mar. 1996 16:2027-2033.
Leutgeb et al., "Pattern separation in the dentate gyrus and CA3 of the hippocampus," Science, Feb. 2007, 315:961-966.
Lissek et al., "Overgeneralization of conditioned fear as a pathogenic marker of panic disorder," Am J Psychiatry, Jan. 2010, 167:47-55.
Marr, "Simple memory: a theory for archicortex," Philosophical transactions of the Royal Society of London, Jul. 1971, 262:23-81.
Massa et al., "Conditional reduction of adult neurogenesis impairs bidirectional hippocampal synaptic plasticity," PNAS, 2011, 108:6644-6649.
Matsuda et al., "abLIM3 is a novel 15 component of adherens junctions with actin-binding activity," European Journal of Cell Biology, Nov. 2010, 89:807-816.
McBain, "Differential mechanisms of transmission and plasticity at mossy fiber synapses," Prog Brain Res, 2008, 169:225-240.
McClelland and Goddard, "Considerations arising from a complementary learning systems perspective on hippocampus and neocortex," Hippo Campus, 1996, 6: 654-665.
McHugh et al., "Dentate Gyrus NMDA Receptors Mediate Rapid Pattern Separation in the Hippocampal Network," Science, Jul. 2007, 317:94-99.
McNaughton and Morris, "Hippocampal synaptic enhancement and information storage within a distributed memory system," Trends Neurosci, 1987, 10:408-415.
Mori et al., "Recruitment of an inhibitory hippocampal network after bursting in a single granule cell," Proc Natl Acad Sci, 2007, 104:7640-7645.
Motley and Kirwan, "A parametric investigation of pattern separation processes in the medial temporal lobe," J Neurosci, Sep. 2012, 32:13076-13085.
Nakashiba et al., "Young dentate granule cells mediate pattern separation, whereas old granule cells facilitate pattern completion," Cell, Mar. 2012, 149: 188-201.
Nakazawa et al., "Requirement for hippocampal CA3 NMDA receptors in associative memory recall," Science, 2002, 297:211-218.
Niibori et al., "Suppression of adult neurogenesis impairs population coding of similar contexts in hippocampal CA3 region," Nature Communications, 2012, 3: 1253.
O'Reilly and McClelland, "Hippocampal conjunctive encoding, storage, and recall: avoiding a tradeoff," Hippocampus, Dec. 1994 4:661-682.
Peri et al., "Psychophysiologic assessment of aversive conditioning in posttraumatic stress disorder," Biol Psychiatry, 2000, 7:512-519.
Piatti et al., "Neurogenesis in the dentate gyrus: carrying the message or dictating the tone," Front Neurosci, 2013, 7:50.
Rolls and Kesner, "A computational theory of hippocampal function, and empirical tests of the theory," Prog Neurobiol, 2006, 79:1-48.
Rolls, "A theory of hippocampal function in memory," Hippocampus, 1996, 6:601-620.
Ruediger et al., "Goal-oriented searching mediated by ventral hippocampus early in trial-and-error learning," Nat Neurosci, 2012.
Ruediger et al., "Learning-related feedforward inhibitory connectivity growth required for memory precision," Nature, 2011, 473:514-518.
Sahay et al., "Increasing adult hippocampal neurogenesis is sufficient to improve pattern separation," Nature, Apr. 2011, 472:466-470.
Sauerhofer et al., "Generalization of contextual fear depends on associative rather than non-associative memory components," Behav Brain Res, Aug. 2012, 233:483-493.
Saxe et al., "Ablation of hippocampal neurogenesis impairs contextual fear conditioning and synaptic plasticity in the dentate gyrus," PNAS, 2006, 103: 17501-17506.
Schmidt-Hieber et al., "Enhanced synaptic plasticity in newly generated granule cells of the adult hippocampus," Nature, 2004, 429: 184-187.
Scobie et al., "Kruppel-like factor 9 is necessary for late-phase neuronal maturation in the developing dentate gyrus and during adult hippocampal neuro genesis," J Neurosci, 2009, 29:9875-9887.
Small et al., "A pathophysiological framework of hippocampal dysfunction in ageing and disease," Nat Rev Neurosci, 2011, 12:585-601.
Small et al., "Imaging correlates of brain function in monkeys and rats isolates a hippocampal subregion differentially vulnerable to aging," PNAS, May 2004, 101:7181-7186.
Smith et al., "3-D reconstruction of the cholinergic basal forebrain system in young and aged rats," Neurobiol Aging, Jul.-Aug. 1993, 14:389-392.
Smith et al., "Circuit-specific alterations in hippocampal synaptophysin immunoreactivity predict spatial learning impairment in aged rats," J Neurosci, Sep. 2000, 20:6587-6593.
Snyder, "Effects of adult neurogenesis on synaptic plasticity in the rat dentate gyrus," J Neurophysiol, Jun. 2001, 85:2423-2431.
Stanley and Shetty, "Aging in the rat hippocampus is associated with widespread reductions in the number of glutamate decarboxylase-67 positive interneurons but not interneuron degeneration," J Neurochem, 2004, 89:204-216.
Stark et al., "A task to assess behavioral pattern separation (BPS) in humans: Data from healthy aging and mild cognitive impairment," Neuropsychologia, Oct. 2013, 51: 2442-2449.
Toner et al., "Visual object pattern separation deficits in nondemented older adults," Learning & Memory, 2009, 16:338-342.
Torborg et al., "Control of CA3 output by feedforward inhibition despite developmental changes in the excitation-inhibition balance," J Neurosci, 2010, 30:15628-15637.
Treves and Rolls, "Computational constraints suggest the need for two distinct input systems to the hippocampal CA3 network," Hippocampus, Apr. 1992, 2:189-199.
Treves et al., "What is the mammalian dentate gyrus good for?," Neuroscience, 2008, 154:1155-1172.
Tronel et al., "Adult-born neurons are necessary for extended contextual discrimination," Hippocampus, 2010, 22: 292-298.
Tsetsenis et al., "Suppression of conditioning to ambiguous cues by pharmacogenetic inhibition of the dentate gyrus," Nat Neurosci, 2007, 10:896-902.
Vanni-Mercier et al., "The hippocampus codes the uncertainty of cue-outcome associations: an intracranial electrophysiological study in humans," J Neurosci, Apr. 2009, 29:5287-5294.
Villeda et al., "The ageing systemic milieu negatively regulates neurogenesis and cognitive function," Nature, 2011, 477:90-94.
Wang et al., "Selective identification of hedgehog pathway antagonists by direct analysis of smoothened ciliary translocation," ACS Chemical Biology, 2012, 7: 1040-1048.
Wang et al., "The precision of remote context memories does not require the hippocampus," Nat Neurosci, 2009, 12:253-255.

(56) References Cited

OTHER PUBLICATIONS

Wilson et al., "Age-associated alterations of hippocampal place cells are subregion specific," J Neurosci, 2005, 25:6877-6886.

Wiltgen and Silva, "Memory for context becomes less specific with time," Learning & Memory, 2007, 14:313-317.

Xu and Sudhof, "A neural circuit for memory specificity and generalization," Science, Mar. 2013, 339: 1290-1295.

Yassa et al., "Pattern separation deficits associated with increased hippocampal CA3 and dentate gyrus activity in nondemented older adults," Hippocampus, Sep. 2011, 21 :968-979.

Yassa et al., "Ultrahigh-resolution microstructural diffusion tensor imaging reveals perforant path degradation in aged humans in vivo," PNAS, 2010, 107:12687-12691.

Yassa, "Age-related memory deficits linked to circuit-specific disruptions in the hippo campus," PNAS, May 2011, 108:8873-8878.

Yehuda and LeDoux, "Response variation following trauma: a translational neuroscience approach to understanding PTSD," Neuron, 2007, 56:19-32.

International Search Report and Written Opinion dated Jul. 21, 2015 in international application No. PCT/US2015/020540, 14 pgs.

Barrientos et al., "Two Novel Members of the ABLIM Protein Family, ABLIM-2 and -3, Associate with STARS and Directly Bind F-actin," J Biol Chem. 2007, vol. 282(11), p. 8393-8403.

Chow et al., "Serum response factor and myocardin mediate arterial hypercontractility and cerebral blood flow dysregulation in Alzheimer's phenotype," Proc Natl Acad Sci USA. 2007, vol. 104(3), p. 823-828.

Sahay et al., "Pattern Separation: A Common Function for New Neurons in Hippocampus and Olfactory Bulb," Neuron. 2011, vol. 70(4), p. 582-588.

Ally et al., "Pattern Separation and Pattern Completion in Alzheimer's Disease: Evidence of Rapid Forgetting in Amnestic Mild Cognitive Impairment," Hippocampus. 2013, vol. 23(12), p. 1246-1258.

Weiner et al., "Military risk factors for Alzheimer's disease," Alzheimers Dement. 2013, vol. 9(4), p. 445-451.

Yamamoto et al., "Therapeutic potential of inhibition of the NF-kB pathway in the treatment of inflammation and cancer," J Clin Invest. 2001, vol. 107(2), p. 135-142.

\* cited by examiner

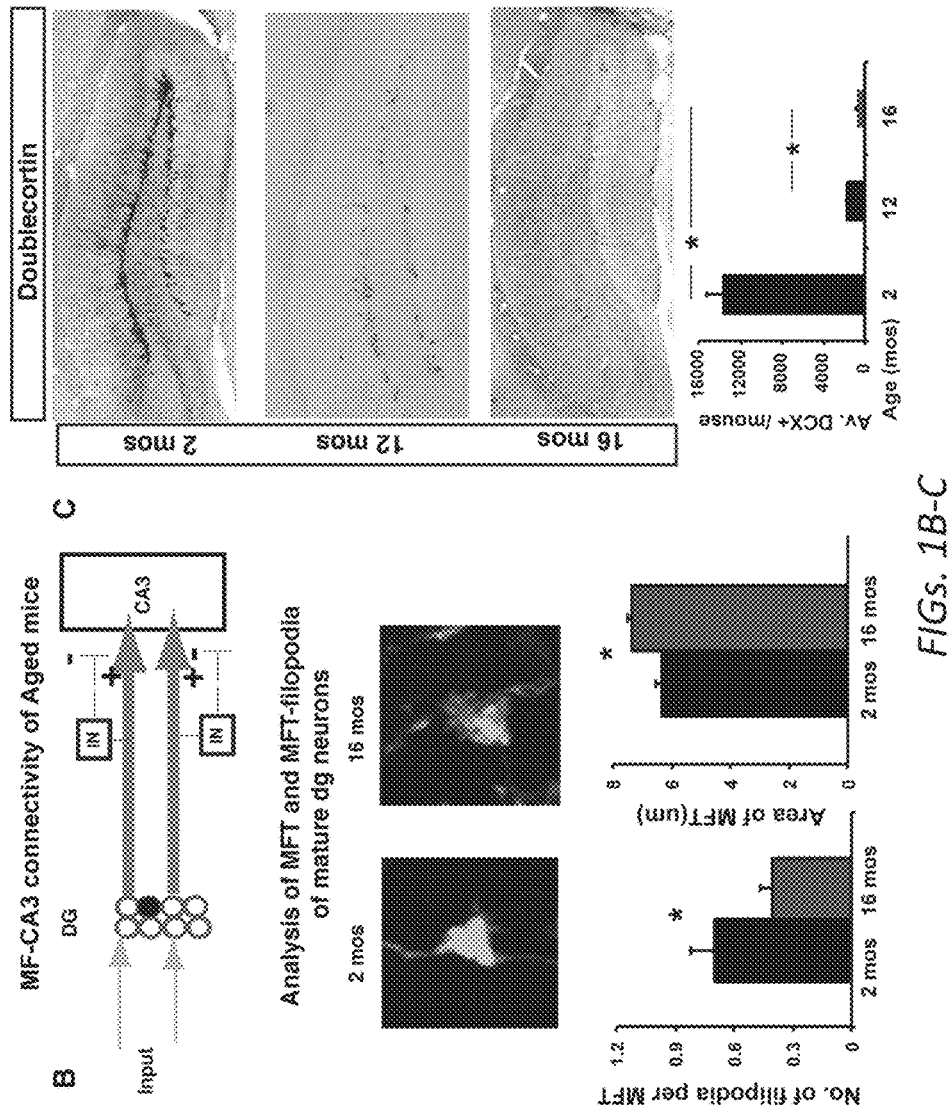
FIGs. 1B-C

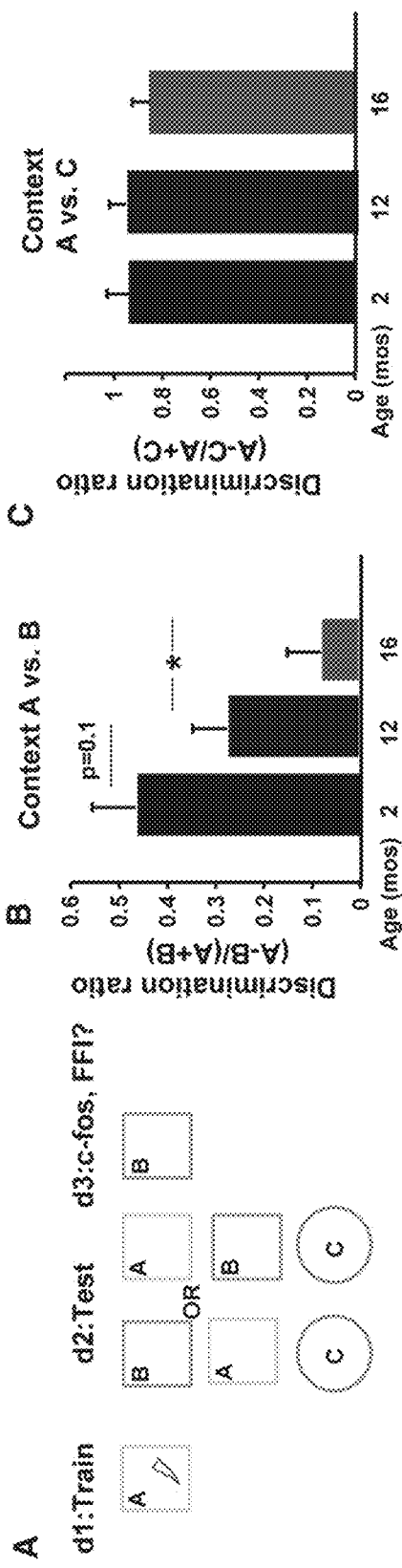
FIGs. 2A-C

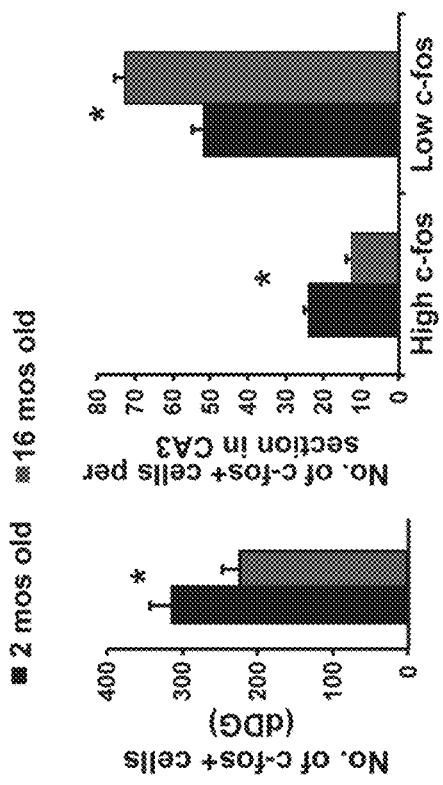
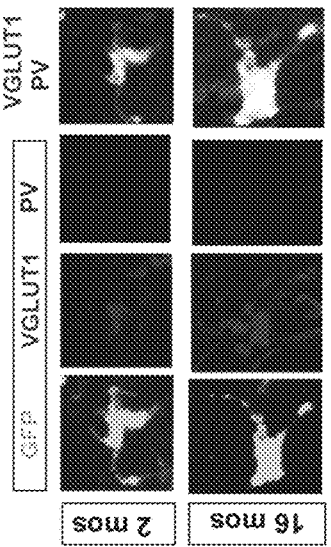
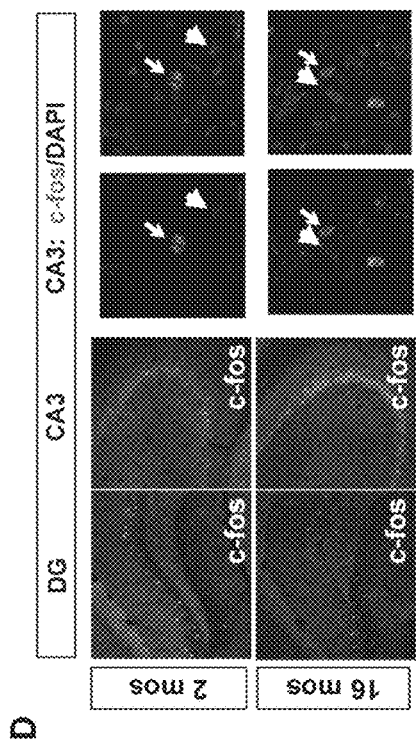
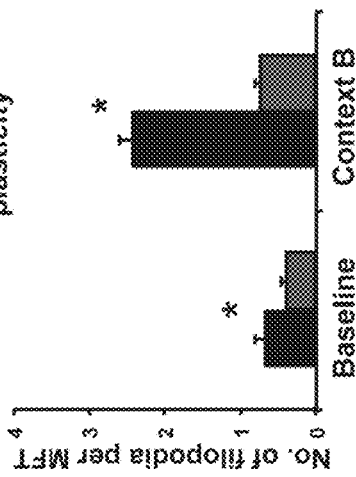
FIGs. 2D-F

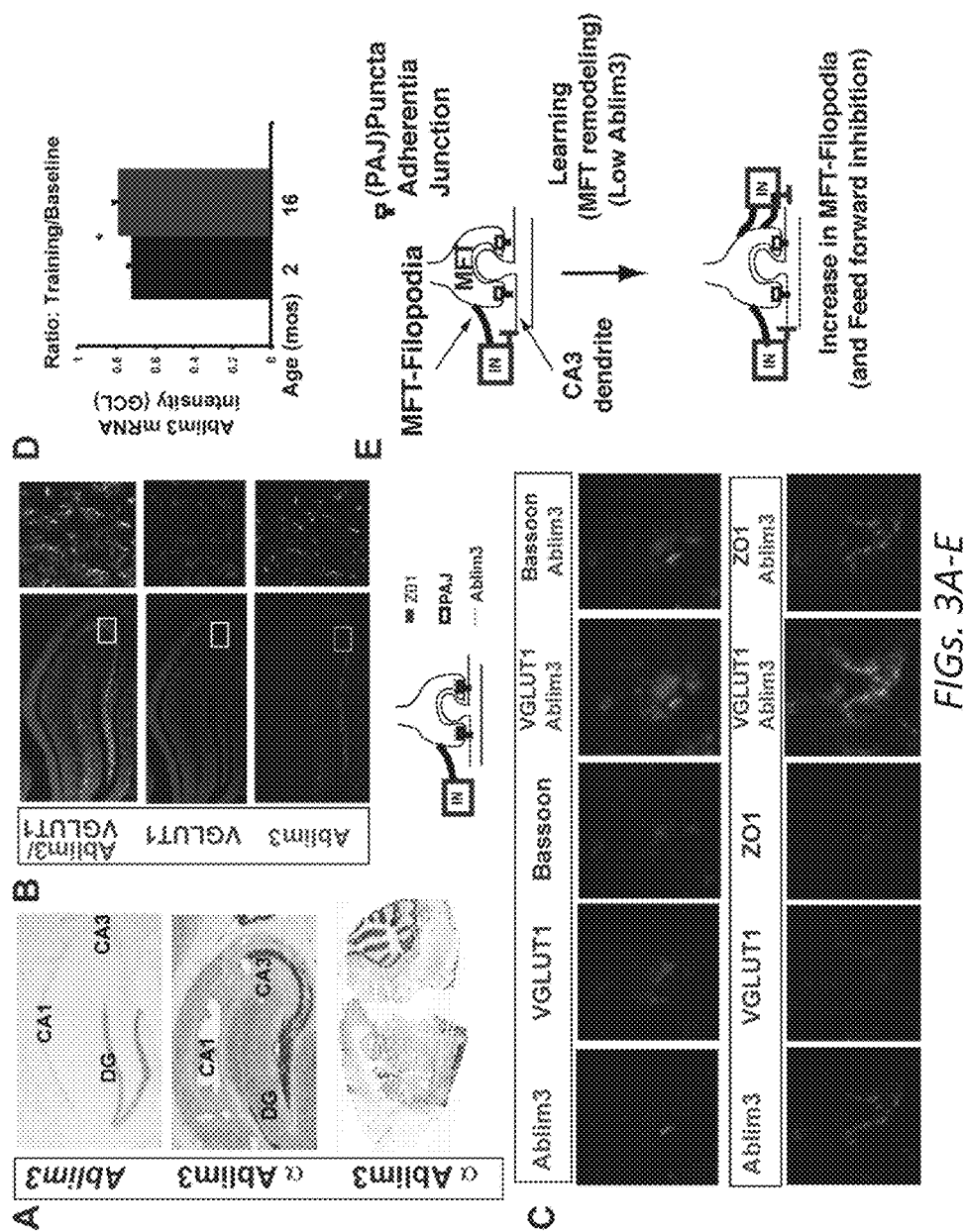
FIGs. 3A-E

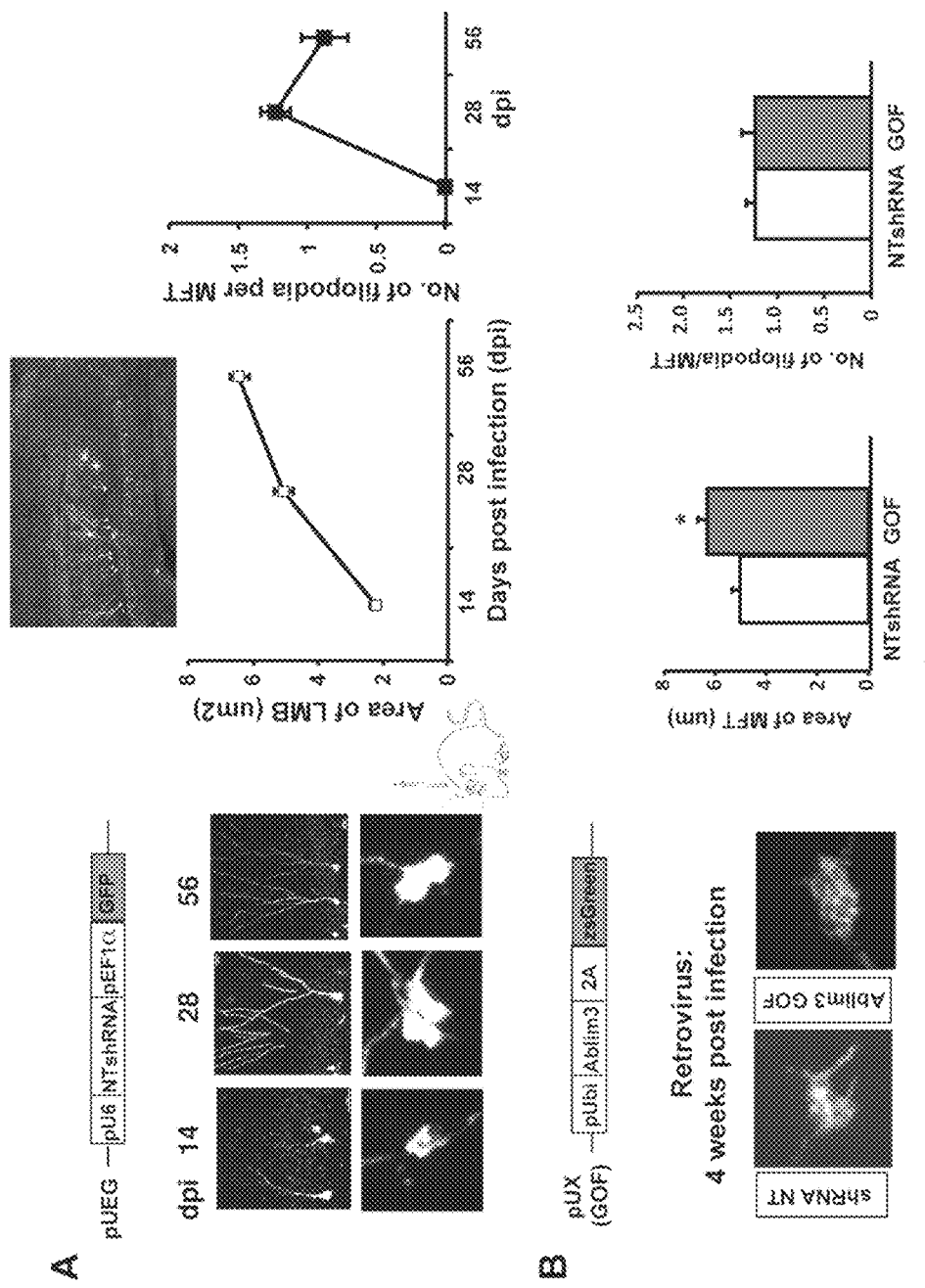
FIGs. 4A-B

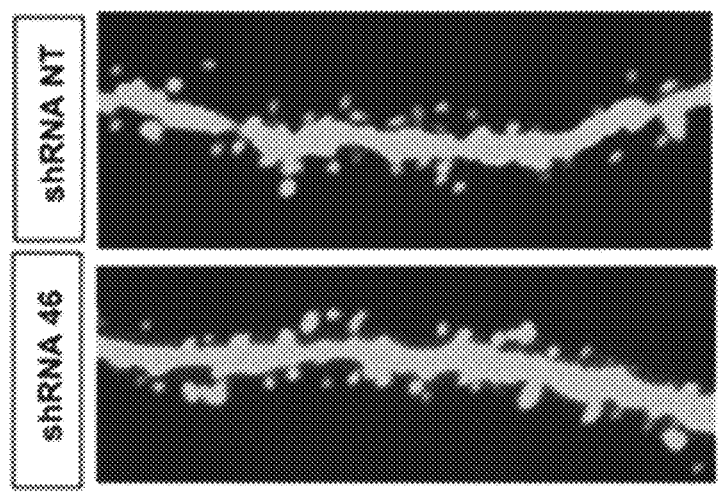
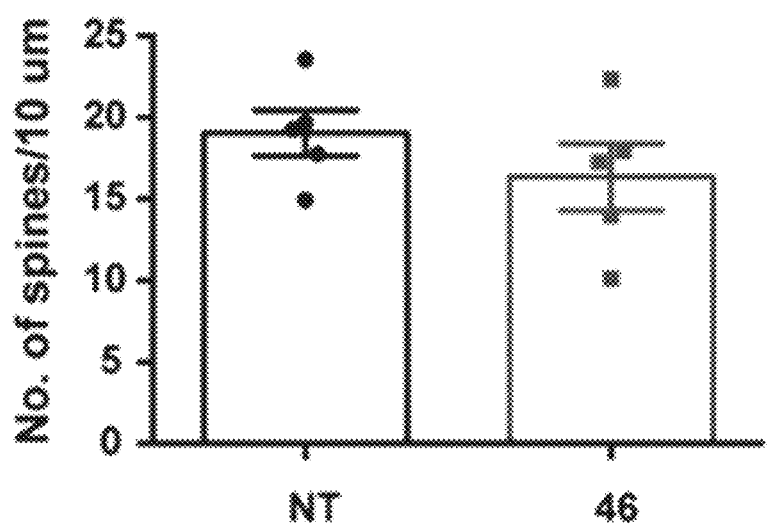
FIG. 5C

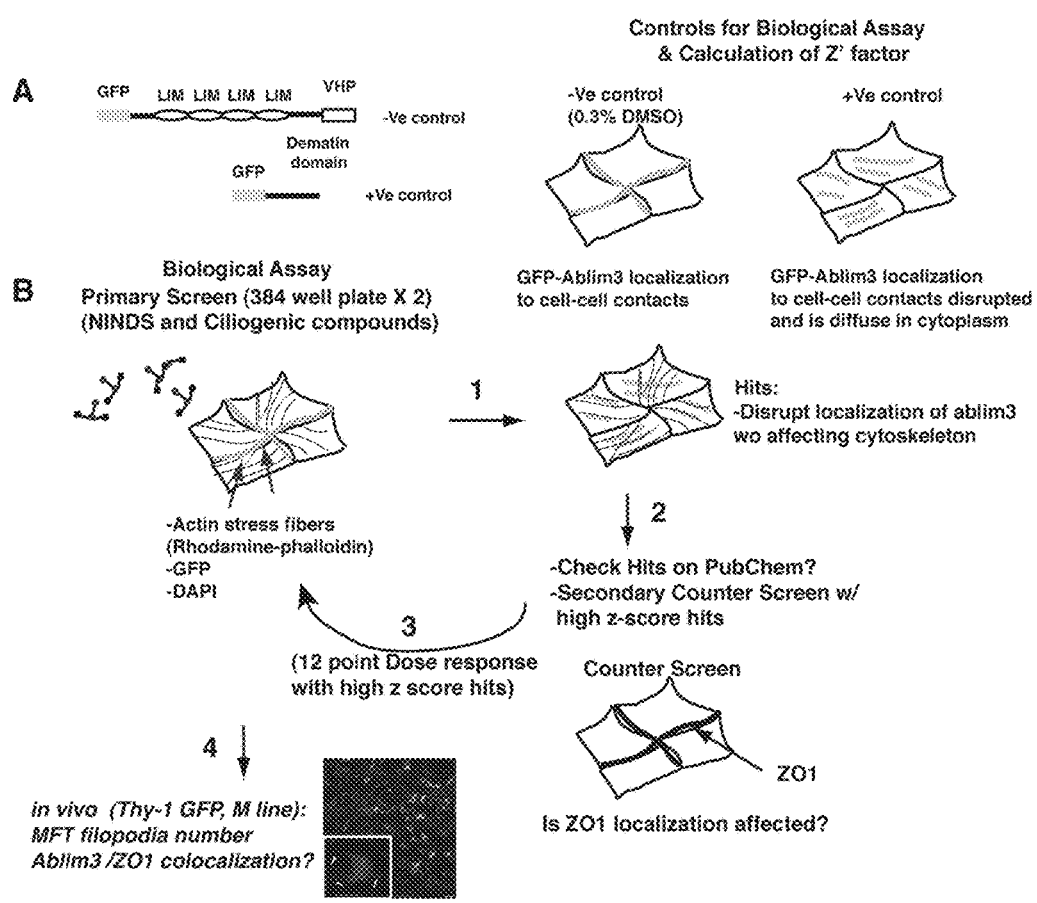
FIGs. 6A-B

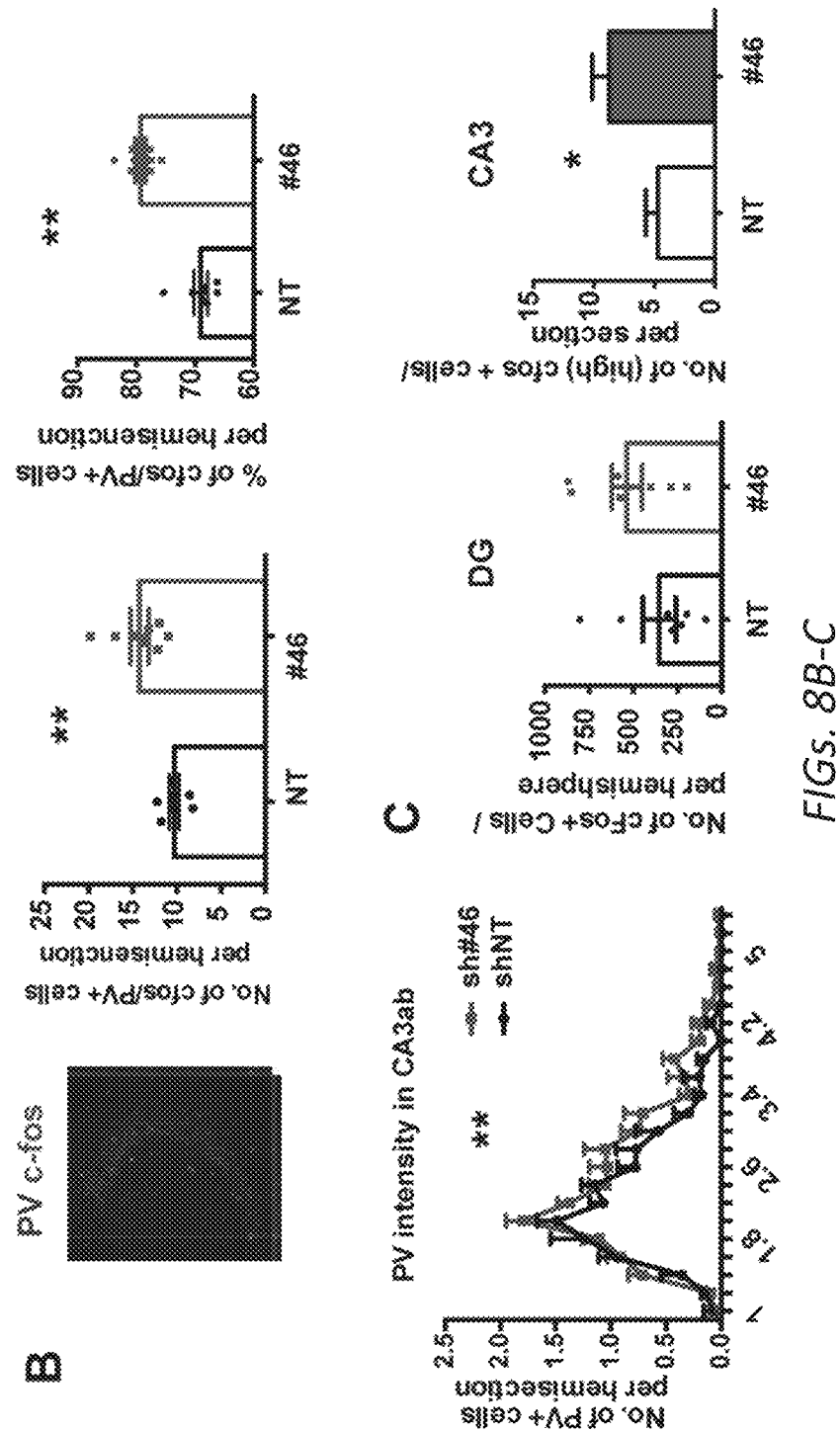
FIGS. 8B-C

MOLECULAR RE-ENGINEERING OF EXCITATION-INHIBITION BALANCE IN MEMORY CIRCUITS

CLAIM OF PRIORITY

This application is the National Stage under 371 of International Application No. PCT/US2015/020540, filed on Mar. 13, 2015, which claims the benefit of U.S. Provisional Application Ser. No. 61/952,934, filed on Mar. 14, 2014. The entire contents of the foregoing are incorporated herein by reference.

TECHNICAL FIELD

Described are memory-regulating agents and methods that target actin binding LIM protein family, member 3 (ABLIM3).

BACKGROUND

Central to efforts to developing novel therapeutics for reversing cognitive and mood impairments associated with Alzheimer's Disease (AD), psychiatric illnesses such as PTSD and during normal aging, is identifying the underlying dysfunctional neural circuits and restoring their functional properties.

SUMMARY

As described herein, Ablim3 has been identified as a molecular brake of DG axonal filopodia and functions in enhancing memory strength and precision and pattern separation. Thus described herein are methods of inhibiting Ablim3 using inhibitory nucleic acids that target the Ablim3 gene or mRNA; and a cell-based assay that can be used to screen for small molecule regulators of Ablim3 function, to improve memory in subjects, e.g., subjects with memory dysfunction associated with AD, normal aging, or PTSD.

Thus, provided herein are methods for improving memory in a subject; the methods comprise administering to the subject an effective amount of an inhibitory nucleic acid targeting actin binding LIM protein family, member 3 (ABLIM3).

In some embodiments, the subject has memory dysfunction associated with normal aging or Alzheimer's Disease. In some embodiments, the subject has post-traumatic stress disorder.

In some embodiments, pattern (memory) separation is improved in the subject.

In some embodiments, the inhibitory nucleic acid is 5 to 40 bases in length (optionally 12-30, 12-28, or 12-25 bases in length). In some embodiments, the inhibitory nucleic acid is 10 to 50 bases in length. In some embodiments, the inhibitory nucleic acid comprises a base sequence at least 90% complementary to at least 10 bases of the Ablim3 RNA sequence. In some embodiments, the inhibitory nucleic acid comprises a sequence of bases at least 80% or 90% complementary to, e.g., at least 5-30, 10-30, 15-30, 20-30, 25-30 or 5-40, 10-40, 15-40, 20-40, 25-40, or 30-40 bases of the RNA sequence. In some embodiments, the inhibitory nucleic acid comprises a sequence of bases with up to 3 mismatches (e.g., up to 1, or up to 2 mismatches) in complementary base pairing over 10, 15, 20, 25 or 30 bases of the RNA sequence. In some embodiments, the inhibitory nucleic acid comprises a sequence of bases at least 80% complementary to at least 10 bases of the RNA sequence. In some embodiments, the inhibitory nucleic acid comprises a sequence of bases with up to 3 mismatches over 15 bases of the RNA sequence. In some embodiments, the inhibitory nucleic acid is single stranded. In some embodiments, the inhibitory nucleic acid is double stranded.

In some embodiments, the inhibitory nucleic acid comprises one or more modifications comprising: a modified sugar moiety, a modified internucleoside linkage, a modified nucleotide and/or combinations thereof. In some embodiments, the inhibitory nucleic acid is an antisense oligonucleotide, LNA molecule, PNA molecule, ribozyme or siRNA. In some embodiments, the inhibitory nucleic acid is double stranded and comprises an overhang (optionally 2-6 bases in length) at one or both termini. In some embodiments, the modified internucleoside linkage comprises at least one of: alkylphosphonate, phosphorothioate, phosphorodithioate, alkylphosphonothioate, phosphoramidate, carbamate, carbonate, phosphate triester, acetamidate, carboxymethyl ester, or combinations thereof. In some embodiments, the modified sugar moiety comprises a 2'-O-methoxyethyl modified sugar moiety, a 2'-methoxy modified sugar moiety, a 2'-O-alkyl modified sugar moiety, or a bicyclic sugar moiety. In some embodiments, the inhibitory nucleic acid comprises one or more of 2'-OMe, 2'-F, LNA, PNA, FANA, ENA or morpholino modifications.

In some embodiments, the inhibitory nucleic acid is selected from the group consisting of antisense oligonucleotides, ribozymes, external guide sequence (EGS) oligonucleotides, siRNA compounds, micro RNAs (miRNAs); small, temporal RNAs (stRNA), and single- or double-stranded RNA interference (RNAi) compounds.

In some embodiments, the RNAi compound is selected from the group consisting of short interfering RNA (siRNA); or a short, hairpin RNA (shRNA); small RNA-induced gene activation (RNAa); and small activating RNAs (saRNAs).

In some embodiments, the antisense oligonucleotide is selected from the group consisting of antisense RNAs, antisense DNAs, and chimeric antisense oligonucleotides.

Also provided herein are methods for identifying a candidate small molecule inhibitor of Ablim3. The methods include providing a test sample comprising a population of cells that express Ablim3; contacting the sample with a test compound; detecting subcellular localization of Ablim3 protein in the cells in the presence of the test compound; determining whether the Ablim3 protein is localized to adherens junctions in the cells in the presence of the cells; selecting as a candidate inhibitor a test compound that reduces localization of Ablim3 protein to adherens junctions.

In some embodiments, the cells express an Ablim3 reporter construct, wherein Ablim3 is linked to a detectable label, preferably a fluorescent protein.

In some embodiments, the methods include evaluating actin cytoskeleton in the cells, and selecting as a candidate inhibitor a test compound that reduces localization of Ablim3 protein to adherens junctions and does not disrupt the actin cytoskeleton In some embodiments, the methods include administering a candidate compound to an animal model; evaluating an effect of the candidate compound on memory in the animal model; and selecting a compound that improves memory in the animal model.

In some embodiments, the compound improves pattern separation in the animal model.

In some embodiments, the test compound is a polypeptide, polynucleotide, inorganic large or small molecule, or organic large or small molecule.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-C. Increased FFE-FFI ratio and decreased adult hippocampal neurogenesis in aging. A-B. Wiring diagram and anatomical labeling showing segregation of FFI and FFE in MFTs and MFT-filopodia (red asterisks) in DG-CA3 circuit in adulthood and aging. Line thickness conveys strength. Activation of CA3 neurons in contexts A and B conveys global remapping. C. Reduced MFT-filopodia, increased MFT size, and decreased adult hippocampal neurogenesis in aged mice (C). n>50 MFTs (B) and n=3-4 mice/gp (B-C). Data are mean+/−S.E.M. *p<0.05.

FIGS. 2A-F. Aged mice show impaired contextual discrimination precision, increased CA3 activation during retrieval, and dampened learning-induced enhancement of FFI connectivity. A. Experimental design for behavioral testing and analysis of circuit activation and FFI connectivity. B-C. Assessment of encoding and memory precision in adult, middle aged and aged mice using a contextual fear discrimination learning paradigm. D. c-fos immunohistochemistry following exposure to context B. Aged mice show increased number of low c-fos+ve cells (arrowheads) and fewer high c-fos+ cells (arrows) in CA3 compared to adult mice. DG activation is lower in aged mice. E-F. Aged mice fail to show potentiation of MFT-filopodial contacts with SL PV+ interneurons following learning (after context B). n=10-12 mice/gp (B-C), n=4-6 mice/gp, subset of mice used in B-C (D), n=4-6 mice/gp (E-F), n>50 MFTs. Data are mean+/−S.E.M. *p<0.05.

FIGS. 3A-E. Ablim3 colocalizes to PAJs within MFTs and a model showing how Ablim3 levels dictate MFT stabilization, MFT remodeling and MFT-filopodial number. A. ISH and immunohistochemistry for Ablim3 in adult hippocampus and whole brain sections. B-C. Ablim3 localizes to PAJs (ZO1+), but not active zones (Bassoon+), within MFTs (VGLUT1+). D. Ablim3 expression is increased in aged mice following CFD. E. Model for how Ablim3 levels dictate MFT remodeling and MFT-filopodial number. n=4-6 mice/gp (D). Data are mean+/−S.E.M. *p<0.05.

FIGS. 4A-B. Analysis of FFE and FFI connectivity during adult-born dg neuronal maturation and molecular control of FFE connectivity in adult-born dg neurons. A. 4 weeks old adult-born neurons show highest MFT-filopodia number and MFT size increases with maturation. Inset: Retroviral labeled adult-born dg neurons of different ages, MFTs and low magnification of DG-CA3. B. Ablim3 overexpression in 4 weeks old adult-born neurons increases MFT size. At least n=50 MFTs and n=3 mice per timepoint (A-B). Data are mean+/−S.E.M. *p<0.05.

FIGS. 5A-F Ablim3 down regulation in dg neurons in adult and aged mice increases FFI connectivity. A. Characterization of shRNAs targeting Ablim3. Western blot and Ablim3 immunohistochemistry showing complete knockdown of Ablim3 in 293T cells in vitro and in vivo with shRNAs 46 and 47. B. Schematic of lentiviral construct used for Ablim3 knockdown in vivo. Representative images of MFTs from adult (3mos) mice injected with NTshRNA or shRNA46. shRNA46 expressing MFTs have multiple VGLUT1+ filopodia that contact PV interneurons in CA3ab. Quantification of MFT size, MFT filopodia number and length. C. Quantification of dg neuronal dendritic spine density following lentiviral mediated Ablim3 knockdown. D-E. shRNA 46 increases MFT-filopodia number in mature dg neurons of aged (16 mos) mice without changing dendritic spine density and size distribution. F. Retroviral downregulation of Ablim3 in just adult-born dg neurons produces long-lasting enhancement in FFI connectivity (MFT filopodia). At least n=50 MFTs and n=3 mice per construct. *p<0.05, Data are mean+/−S.E.M.

FIGS. 6A-B show (A) GFP-Ablim3 constructs used to generate stable cell lines (−ve and +ve controls). B, a flowchart for primary and secondary screens. White arrows indicate MFT filopodia in Thy-1 GFP, M line.

FIGS. 8A-C. A. Representative images of viral injections of shRNA (NT and #46) into DG of 16 months old aged mice. Experimental design and quantification of long-term contextual fear memory. B. Ablim3 downregulation enhances activation of stratum lucidum-PV interneurons and PV expression levels. C. CA3ab of shRNA #46 mice shows increased c-fos (High) whereas DG activation is unchanged. N=10-12 mice/group. *p<0.05, **p<0.01. PV intensity significance (Repeat Measures ANOVA). Data are mean+/−S.E.M.

DETAILED DESCRIPTION

Figure 1A:
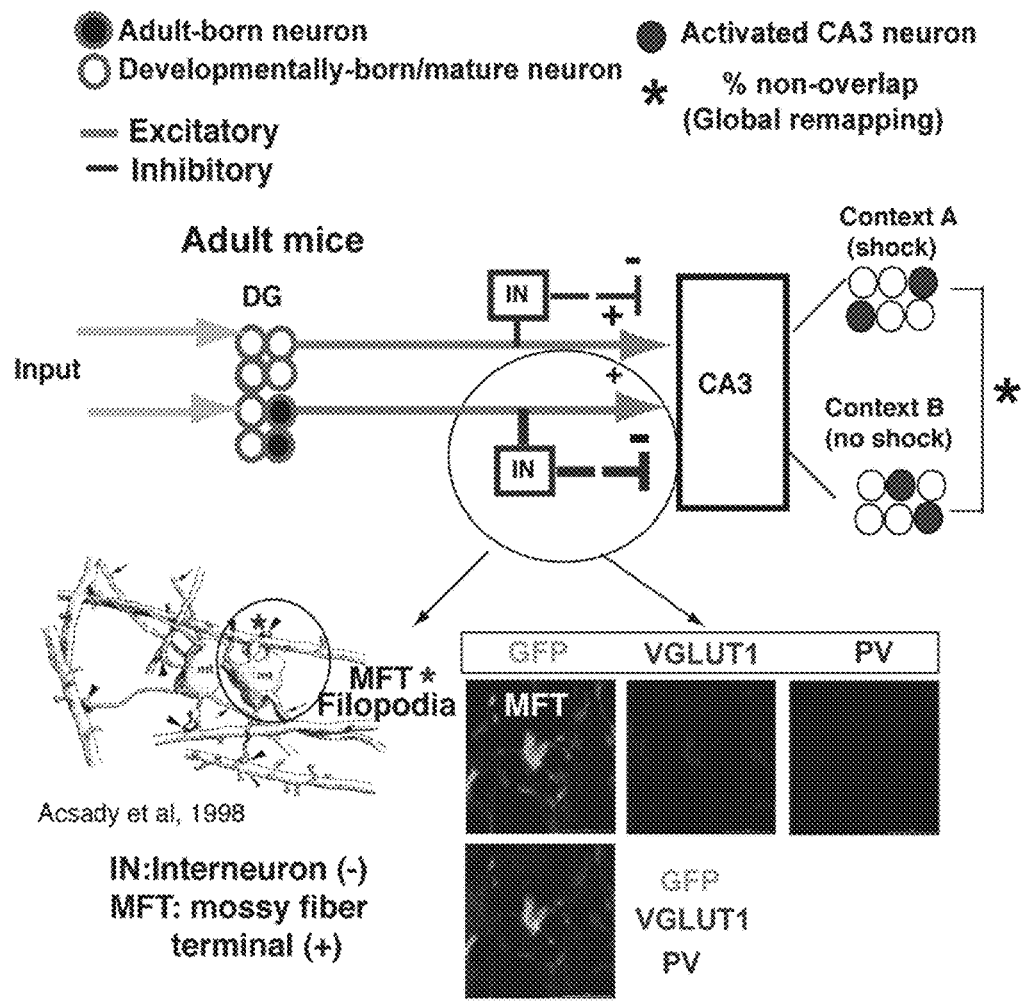

The dentate gyrus (DG)-CA3 circuit is the one of the only regions in the adult mammalian brain that is host to neurogenesis, a process by which stem cells generate new neurons. The DG-CA3 circuit plays a critical role in assessing if our day-to-day experiences are different from those previously encountered, a process known as pattern separation. Pattern separation is essential to formation of new memories of places and events and is impaired during early stages of AD, normal aging and potentially, in post-traumatic stress disorder (PTSD). As shown herein, adult hippocampal neurogenesis is indispensable for pattern separation suggesting that it may be harnessed to reverse pattern separation impairments in the pathological brain. The wiring diagram of the DG-CA3 circuit suggests a role for specialized structures called axonal filopodia on synaptic terminals of DG neurons that modulate levels of inhibition in the circuit and influence pattern separation. However, the capacity to generate new axonal filopodia becomes progressively restricted with neuronal maturation and only during learning, is axonal filopodia-dependent structural plasticity dramatically increased. Without wishing to be bound by theory, it is hypothesized that molecular brakes that facilitate synaptic stabilization are regulated to destabilize synapses and enhance axonal filopodial plasticity, memory strength and precision and and pattern separation. Targeting these molecular brakes is expected to enhance memory strength and precision and pattern separation by rejuvenating structural plasticity of axonal filopodia of adult-born neurons and older neurons in the DG-CA3 circuit. Here, Ablim3 is identified as a molecular brake of DG axonal filopodia and functions in enhancing memory strength and precision and pattern separation. Thus described herein are methods of inhibiting Ablim3 using inhibitory nucleic acids that target the Ablim3 gene or mRNA; and a cell-based assay that can be used to screen for small molecule regulators of Ablim3 function.

Targeting FFE-FFI Balance to Enhance Memory in Normal Aging and AD

Aging affects multiple memory systems in the brain and a constellation of cognitive processes normally subserved by these brain regions (Hof and Morrison, 2004). These include impaired ability to form new episodic memories, spatial navigation, and contextual source memory (Small et al., 2011). The development of effective procognitive interventions for aging necessitates understanding how specific neural circuits within the medial temporal lobe contribute to each of these different memory functions. Episodic memory formation requires a balance of two distinct mnemonic processes, pattern separation and pattern completion in the DG-CA3 circuit of the hippocampus. Whereas, pattern separation in DG is essential to distinguish between similar experiences by minimizing interference (Treves and Rolls, 1992; O'Reilly and McClelland, 1994; McClelland and Goddard, 1996; Rolls, 1996; Gilbert et al., 2001; Leutgeb et al., 2007; McHugh et al., 2007; Bakker et al., 2008), pattern completion in CA3 facilitates the retrieval of memories based on partial cues (Marr, 1971; McNaughton and Morris, 1987; Nakazawa et al., 2002). Rodent studies suggest that pattern separation-completion balance is disrupted in aging. At a cellular level this manifests as inflexible encoding of similar environments by independent neuronal ensembles or impaired global remapping and elevated CA3 place cell firing (Wilson et al., 2005). At a behavioral level, contextual discrimination and spatial pattern separation is impaired (Creer et al., 2010)(FIG. 2). Interestingly, aged humans and individuals with mild cognitive impairment (MCI) show increased activation of CA3 circuitry during retrieval (Bakker et al., 2012) and impaired discrimination of perceptually similar objects (Toner et al., 2009; Yassa et al., 2011b; Yassa et al., 2011a; Bakker et al., 2012; Stark et al., 2013). Despite this evidence for altered DG-CA3 circuit function in aging, the precise underlying neurobiological mechanisms are poorly understood. Aging related changes in the medial temporal lobe system (MTL) include reduction in perforant path (PP) inputs (Geinisman et al., 1992; Smith et al., 2000; Hof and Morrison, 2004; Yassa et al., 2010), hippocampal neurogenesis (Kuhn et al., 1996; Villeda et al., 2011)(FIG. 1), expression of glutamate decarboxylase-67 in interneurons (Stanley and Shetty, 2004) and alterations in the cholinergic system (Decker, 1987; Smith et al., 1993). Although reduced PP-DG connectivity and altered cholinergic inputs to CA3 has been proposed to result in lower inhibition onto CA3 pyramidal neurons and consequently, hyperactivation and excessive pattern completion through their highly recurrent collaterals during retrieval (Hasselmo et al., 1995; Wilson et al., 2005), causal evidence linking changes in excitation-inhibition (E-I) balance and age-related changes in CA3 properties and pattern separation-completion imbalance is conspicuously absent.

As demonstrated herein, a reduction in feed-forward inhibition (FFI) and increase in feed forward excitation (FFE) in DG-CA3 circuitry causally relates to excessive CA3 activation during retrieval and pattern separation-completion imbalance in the aged brain. Importantly, a novel molecular mechanism has been identified by which connectivity underlying FFI and FFE in DG-CA3 circuitry can be selectively modulated to causally assess how changes in FFE and FFI link with CA3 properties and encoding and memory precision. Since changes in FFI in DG-CA3 are downstream to reduction in PP-DG inputs in aging, restoring FFI in DG-CA3 may offset decreased PP-dependent activation of DG to reverse pattern separation-completion imbalance and CA3 hyperactivation during retrieval.

Although altered E-I balance in the MTL (EC-DG-CA3 circuits) has been proposed to contribute to altered CA3 properties in aging (Wilson et al., 2005), causal evidence is absent owing to a lack of tools that selectively target E-I balance in this circuit without affecting other neuronal and circuit properties. We have identified age related changes in connectivity underlying FFE and FFI in the DG-CA3 circuit and increased CA3 activation in aging that accompanies loss of contextual encoding and memory precision (FIG. 1, 2). FFI has been suggested to facilitate sparse coding and modulate excitation of the recurrent collateral circuitry of CA3, features long recognized as conducive to pattern separation-completion balance (Treves and Rolls, 1992) (O'Reilly and McClelland, 1994; Bragin et al., 1995) (McClelland and Goddard, 1996) (Acsady and Kali, 2007; Torborg et al., 2010; Ikrar et al., 2013; Piatti et al., 2013) (McBain, 2008). Furthermore, FFI connectivity has been implicated in encoding and memory precision (Ruediger et al., 2011; Ruediger et al., 2012). Motivated by these observations, a screen was performed to identify selective molecular regulators of FFE and FFI connectivity in the DG-CA3 circuit. The screen took advantage of the fact that the DG-CA3 circuit shows exquisite anatomical segregation of FFE and FFI within the MFT (Acsady et al., 1998; McBain, 2008). Specifically, dg neurons make excitatory connections with CA3 neurons via large MFTs and onto parvalbumin (PV) +ve inhibitory interneurons in stratum lucidum (SL) via vesicular glutamate transporter-1 (VGLUT1) +ve filopodia emanating from the MFTs (referred to as MFT-filopodia) (FIG. 1A). Since these interneurons inhibit CA3 neurons, the synaptic connections of MFT-filopodia and MFTs influence E-I balance and activation of the CA3 recurrent collateral circuitry underlying pattern completion. Moreover, learning increases MFT-filopodia number and MFT-filopodia number correlates tightly with encoding and memory precision (Ruediger et al., 2011; Ruediger et al., 2012). Therefore, we wanted to identify factors that regulate MFT-filopodia and MFT size, respectively without affecting dendritic spine density or input specificity. We identified Ablim3 as one such factor which is exclusively localized to mossy fiber terminals (MFTs) and is absent from hilar mossy cells, interneurons, and hippocampal molecular layers. Importantly, Ablim3 acts as brake on structural plasticity of MFTs (FIG. 3, 4). Using newly developed retroviral and lentiviral expression systems to downregulate or overexpress Ablim3 in dentate granule (dg) neurons, we found that we can increase the number of MFT-filopodial contacts with PV+ interneurons or MFT size, respectively, without changing dendritic spine density (FIG. 4, 5). Since Ablim3 functions through its localization at MFT-CA3 spine contact sites known as puncta adherens junctions (PAJs) within MFTs and because MFTs in the hilus lack PAJs (Acsady et al., 1998), viral regulation of Ablim3 expression levels in dg neurons should selectively impact FFI and FFE without changing feed-back inhibition onto DG. Thus, we have identified one of the first molecular regulators of FFI-FFE balance in the DG-CA3 circuit that diametrically dictates MFT size and MFT-filopodial contacts with interneurons without affecting input specificity of dg neurons.

Targeting FFE-FFI Balance to Enhance Ambiguous Threat Processing

The generation of adaptive fear responses to ambiguous threats in the environment is critically dependent on how contexts and cue-contingency relationships are encoded. Inefficient encoding of ambiguous threats may result in heightened avoidance behavior, overgeneralization of fear, hyper vigilance and arousal, symptoms that characterize anxiety disorders such as PTSD, GAD and panic disorder (Peri et al., 2000; Yehuda and LeDoux, 2007; Grillon et al., 2009; Lissek et al., 2010). Current theories assert that overgeneralization of fear has its origins in time dependent changes in associative learning and decrease in fidelity of the memory (Biedenkapp and Rudy, 2007; Wiltgen and Silva, 2007; Wang et al., 2009; Sauerhofer et al., 2012) or a failure to incorporate details in CA1 during encoding (Xu and Sudhof, 2013). The present inventors propose that efficient discrimination of ambiguous threats arises from minimizing interference between overlapping contextual information or predictors of contingency. One mechanism that fulfills these functions is pattern separation through global remapping, a mnemonic process by which the DG-CA3 circuit disambiguates perceptually similar inputs to constrain the retrieval of previously encoded memories based on partial cues, a process also referred to as pattern completion (Marr, 1971; O'Reilly and McClelland, 1994; Gilbert et al., 2001; Rolls and Kesner, 2006; Leutgeb et al., 2007; McHugh et al., 2007; Bakker et al., 2008; Yassa and Stark, 2011; Motley and Kirwan, 2012). Although work by others and us has implicated adult-born dg neurons in pattern separation (Clelland et al., 2009; Tronel et al., 2010; Sahay et al., 2011b; Nakashiba et al., 2012; Niibori et al., 2012), the circuit mechanisms and neural pathways by which adult-born neurons process ambiguous threats is not known. By identifying properties of adult-born dg neurons instrumental to encoding, we may be able to target these properties in not just adult-born dg neurons, but also rejuvenate mature dg neurons and reengineer DG-CA3 circuitry to modulate pattern separation.

Methods of Treatment

Thus, described herein are methods of treating memory dysfunction in subjects in need thereof, e.g., in subjects with memory dysfunction relating to normal or abnormal aging (e.g., AD), or in subjects with anxiety disorders such as PTSD, GAD and panic disorder. Generally, the methods include administering a therapeutically effective amount of an inhibitor of Ablim3 as described herein, to a subject who is in need of, or who has been determined to be in need of, such treatment.

As used in this context, to "treat" means to ameliorate at least one symptom of the disorder associated with memory dysfunction. For example, a treatment can result in a reduction in memory lapses and a return or approach to normal memory. Administration of a therapeutically effective amount of a compound described herein for the treatment of anxiety disorders will result in decreased anxiety.

In some embodiments, the inhibitor of Ablim 3 is an inhibitory nucleic acid that is complementary to Ablim3. Exemplary inhibitory nucleic acids for use in the methods described herein include antisense oligonucleotides and small interfering RNA, including but not limited to shRNA and siRNA. The sequence of Ablim3 is known in the art; in humans, there are 4 iso forms:

| Isoform | Nucleic Acid | Protein | Notes |
| --- | --- | --- | --- |
| Isoform 1, variant 1 | NM_001301015.1 | NP_001287944.1 | variant (1) represents the longest transcript and encodes the longest isoform (1). Both variants 1 and 2 encode the same isoform 1 |
| Isoform 1, variant 2 | NM_014945.3 | NP_055760.1 | variant (2) lacks an internal segment in the 5' UTR, compared to variant 1. Both variants 1 and 2 encode the same isoform 1. |
| Isoform 2, variant 3 | NM_001301018.1 | NP_001287947.1 | variant (3) lacks an in-frame exon in the 3' coding region, compared to variant 1. The resulting isoform (2) lacks an internal segment, compared to isoform 1. |
| Isoform 3, variant 4 | NM_001301027.1 | NP_001287956.1 | variant (4) has an additional exon in the 5' region, which results in translation initiation at a downstream start codon, and lacks several in-frame in the 3' coding region, compared to variant 1. The resulting isoform (3) has a distinct N-terminus and lacks two internal segments, compared to isoform 1. |
| Isoform 4, variant 5 | NM_001301028.1 | NP_001287957.1 | This variant (5) lacks several in-frame exons and has an alternate splice site in the 3' coding region, compared to variant 1. The resulting isoform (4) lacks two internal segments and has a shorter and distinct C- |

-continued

| Isoform | Nucleic Acid | Protein | Notes |
|---|---|---|---|
| | | | terminus, compared to isoform 1. |

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the Ablim3 sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within an Ablim3 sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/shRNA

In some embodiments, the nucleic acid sequence that is complementary to an Ablim3 RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 rnM) concentrations of $Mg^{2+}$ cofactor. An artificial "RNA ligase" ribozyme has been shown to catalyze the corresponding self-modification reaction with a rate of about 100 $min^{-1}$ In addition, it is known that certain modified hammerhead ribozymes that have substrate binding arms made of DNA catalyze RNA cleavage with multiple turn-over rates that approach 100 $min^{-1}$.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N (CH3)-CH2, CH2-N (CH3)-N (CH3)-CH2 and O—N (CH3)-CH2-CH2 backbones, wherein the native phosphodiester backbone is represented as O—P—O—CH,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5, 177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3$ $OCH_3$, $OCH_3$ $O(CH_2)n$ $CH_3$, $O(CH_2)n$ $NH_2$ or $O(CH_2)n$ $CH_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-$CH_2CH_2OCH_3$, also known as 2'-O-(2-methoxyethyl)] (Martin et al, Helv. Chim Acta, 1995, 78, 486). Other preferred modifications include 2'-methoxy (2'-0-CH3), 2'-propoxy (2'-$OCH_2$ $CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me—C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other hetero substituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me—C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-amino adenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes.

Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077;

5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herien.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kaup-pinen et al., Drug Disc. Today 2(3):287-290 (2005); and Ponting et al., Cell 136(4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylamino ethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising inhibitory nucleic acid sequences designed to target an RNA.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

Methods of Screening Test Compounds

Included herein are methods for screening test compounds, e.g., polypeptides, polynucleotides, inorganic or organic large or small molecule test compounds, to identify agents useful in the treatment of disorders associated with memory dysfunction or anxiety as described herein.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries,* Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, the screen includes a cell-based assay as described herein, e.g., an assay for small molecule disruptors of ablim3 localization at adherens junctions as described in Example 2. For example, a test compound is applied to a test sample, e.g., a population of cells that express Ablim3, e.g., an Ablim3 reporter construct in which Ablim3 is linked in frame to a detectable label (e.g., a fluorescent protein), and one or more effects of the test compound is evaluated. For example, localization of Ablim3 to adherens junctions can be evaluated; molecules that disrupt Ablim3 localization to adherens junctions, but not actin stress fibers, are candidates for inhibiting ablim3 in vivo.

A number of detectable labels are known in the art, including but not limited to, various enzymes, prosthetic groups, fluorescent materials, luminescent materials, chromogenic materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, quantum dots, or phycoerythrin; an example of a luminescent material includes luminol; examples of bioluminescent materials include luciferase, luciferin, and aequorin, and examples of suitable radioactive material include $^{125}$I, $^{131}$I, $^{35}$S, or $^{3}$H. Other labels include colored particles such as colloidal gold or latex beads.

A cilia screen can be used to further validate candidate molecules. For example, shRNAs against ablim3 can be used to assess specificity of the small molecule candidates. If disrupting ablim3-PAJ association confers a loss of function phenotype, then small molecule treatment of ciliated cells that express ablim3 shRNA should not augment cilia number or length.

In some embodiments, the test sample is, or is derived from (e.g., a sample taken from) a patient or an in vivo model of a disorder as described herein. For example, cells from a human patient or an animal model, e.g., a rodent such as a rat, can be used.

A test compound that has been screened by a method described herein and determined to disrupt ablim3-PAJ association can be considered a candidate compound. A candidate compound that has been screened, e.g., in an in vivo model of a disorder, e.g., a rodent model as described herein, and determined to have a desirable effect on the disorder, e.g., on one or more symptoms of the disorder (e.g., on memory), can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

In addition, test compounds identified as "hits" (e.g., test compounds that disrupt ablim3-PAJ association, or that improve memory in an animal model) can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with memory dysfunction as described herein. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an experimental animal, e.g., an animal model of a disorder associated with memory loss, as described herein. The animal can be monitored for a change in the disorder, e.g., for an improvement in a parameter of the disorder, e.g., a parameter related to clinical outcome. In some embodiments, the parameter is memory loss, and an improvement would be improved memory. In some embodiments, the subject is a human, e.g., a human with AD, and the parameter is improvement in memory, decreased frequency of memory lapses, or delayed or slowed progression of memory loss of demetia. In some embodiments, the subject is a human, e.g., a human with an anxiety disorder, and the parameter is improvement in anxiety, or decreased frequency or severity of anxiety episodes or panic attacks, or a decreased association of anxiety-inducing stimuli with anxiety attacks.

EXAMPLES

The invention is further described in the following examples, which do not limit the scope of the invention described in the claims.

Example 1

The following materials and methods were used in this Example
Data Analysis and Statistics.
Statistical analysis will be carried out using StatView software and statistical significance will be assessed by unpaired two-tailed student's t-tests or ANOVA. Significant main effects or interactions were followed up with Fisher's predicted least-square difference post hoc tests where appropriate. Behavioral phenotype differences will be considered significant if an unpaired t-test between the control condition and test groups or ANOVA gives a p-value below 0.05.

Characterization of shRNAs for Ablim3.

Commercially available candidate shRNAs (Dharmacon, 5'-AAACCCAGGGCTGCCTTGGAAAAG-3; SEQ ID NO:1) were screened for ablim3 knockdown efficiency in vitro using a HA-tagged coding sequence of ablim3 that was cloned into the retroviral vector pUX (kindly provided by Dr. Ge, Stony Brook University). shRNA-mediated knockdown efficiency was assessed by co-transfecting expression vector for Ablim3-pUX and shRNAs into 293T cells and using HA-tagged GFP as transfection control. Cells were lysed and subjected to western blot for Ablim3 expression using anti-Ablim3 or anti-GFP (Abeam) antibodies.

Virus Generation and In Vivo Stereotaxic Injections.

Candidate shRNA sequences and non-targeted shRNA sequence were cloned into the retroviral vector pUEG (kindly provided by Dr. Ge). Engineered retroviruses were produced by co-transfection of shRNA-pUEG vectors and VSVG into HEK293gp cells. Virus-containing supernatant was harvested 36, 48 and 60 hours after transfection and concentrated by ultracentrifugation at 25,000 rpm for 1.5 hours as we recently published (Haar et al., 2013). For the lentiviral constructs, shRNAs sequences were cloned into the HapI and XhoI sites of the lentiviral vector pLLX, which contain a GFP protein driven by ubiquitin promoter. The lenti-ablim3IRES GFP construct was made using a LEM-PRA backbone (Zhou et al., 2006). Low titre engineered lentiviruses were produced by co-trans fection of shRNA-pLLX vectors, VSVG and 48.9 into HEK293T cells followed by ultracentrifugation of viral supernatant at 20,000 rpm for 2 hr. Adult and aged C57BL/6 mice were maintained under standard conditions and viruses were stereotaxically injected into the DG at 2 sites (0.5 µl per site at 0.1 µl/min) with the following coordinates: anterioposterior=-2 mm from bregma; lateral=±1.6 mm; ventral=2.5 mm as we recently published (Ikrar et al., 2013). Injection needles were left in place additional 10 minutes after injection to ensure even distribution of the virus. For behavioral analysis, we will scale up virus production to generate high titre viruses. Adult and aged C57BL/6 female mice were obtained from National Institute on Aging.

Confocal Analysis of MFT, MFT-Filopodia and Dendritic Spines.

For quantification of MFTs and MFT-filopodial contacts with PV+ interneurons confocal z-stack images were acquired using a Nikon MR Si confocal laser, a TiE inverted research microscope, and NIS Elements software (Nikon Instruments, 1300 Walt Whitman Road, Melville, N.Y. 11747-3064) as we recently published (Ikrar et al., 2013). Images of CA3ab were taken using a 60× objective at a resolution of 1024×1024 pixels (0.31 µm/px) with pixel dwell time set at 0.5 µm/s and line averaging at 2. Three-dimensional Z-series stacks were captured at 0.5 µm increments with six to eight times optical zoom. For spine imaging, confocal 2.1 uM z-stacks (2048 resolution) with 0.3 uM step size were taken centered on dendritic segment. Imaging was performed using a 60× objective, plus 1.5× optical zoom and 6× digital zoom, using 2× frame averaging at each step to eliminate background. Z-stack were flattened using the maximum intensity projection, and flattened images were quantified using image J. For spine density, spines per measured dendritic length were counted manually, and head diameter (widest point) and length (furthest point from dendrite) were taken for individual spines to calculate spine size distribution.

catFISH.

c-fos CRNA probe was used to assess localization of cytoplasmic RNAs. Nuclear localization was assessed using intronic c-fos probe (kindly provided by Dr. Dayu Lin, NYU) and protocol previously reported (Lin et al., 2011). To assess % non-overlap of activated cells in each context, z-stacks of dorsal CA3ab neurons will be captured and we will quantify the number of CA3 pyramidal neurons that show nuclear, cytoplasmic or nuclear+cytolasmice c-fos following exposure to the second environment using NIH Image J software.

Immunohistochemistry and ISH.

Immunohistochemistry for c-fos, Ablim3, VGLUT1, PV and Z0-1 was performed using protocols reported previously (Ruediger et al., 2011). ISH for ablim3 was done as we have previously reported (Scobie et al., 2009). We quantified c-fos signal intensities from cells in dorsal CA3 in 4 matched sections per mouse. High (above mean) and low (below mean) c-fos signal was based on the mean of population quantified in each section following background subtraction (signal in stratum radiatum). All sections and images used for comparisons were processed in the same experiment and acquired with identical settings, respectively.

Contextual Fear Discrimination.

Contextual fear conditioning was performed using 4 chambers Coulburn apparatus. The protocol entailed delivery of 2 1-second foot shocks of 0.75 mA spaced apart by 60 seconds and 180 seconds following placement in training context. The mouse was taken out 60 seconds following second foot shock and returned to its home cage. No differences in acquisition were seen between aged and adult mice. On testing days, mice were brought out of the vivarium and allowed to habituate for an hour outside the testing room prior to starting the experiment. Mouse behaviour was recorded by digital video cameras mounted above conditioning chambers. The chamber was lit from above with a houselight (CM1820 bulb), ventilated with a house fan and encased by a sound-dampening cubicle. Freezeframe and Freezeview software (Actimetrics, Evanston, Ill.) were used for recording and analyzing freezing behaviour, respectively. For shock associated training context A, the house fan and lights were switched on and stainless steel grids were exposed. 70% ethanol was used to clean grids in between runs. The similar context B had cardboard covering the walls and the grids. The house fan and lights were switched off and the door was left ajar for providing lighting for the camera. Grid-floors were cleaned with tissue without ethanol. Both contexts A and B were housed in Coulburn chambers. Context C was outside the chamber but housed in the same room as the chambers. It is comprised of a paper bucket in a plastic box. Mice were brought into testing room in a red plastic container.

Example 1.1. Increasing FFE Connectivity of Adult-Born dg Neurons in Adult Mice is Sufficient to Produce Aging Related Alterations in CA3 and Encoding and Memory Imprecision Analysis of FFE and FFI connectivity during aging revealed an increase in MFT size and decreased number of VGLUT1+ve MFT-filopodial contacts of mature dg neurons with SL PV+ve interneurons (FIG. 1A-B) in aged mice relative to adult mice. At a behavioral level, aged mice showed impaired discrimination of two similar, but not distinct, contexts compared to adult or middle-aged mice (FIG. 2A-C). Since increased freezing in the similar context (context B) may arise due to excessive pattern completion in CA3, we examined activation of CA3 in adult and aged mice and learning dependent changes in FFI connectivity following exposure to the similar context B. Aged mice showed fewer "high" c-fos expressing cells and more "low" c-fos expressing cells in CA3 compared with adult mice (FIG. 2D). These changes were paralleled by a failure to show robust learning dependent enhancement of FFI connectivity (VGLUT1+ve MFT-filopodial contacts of mature dg neurons with SL PV+ve interneurons) as seen in adult mice (FIG. 2E-F). Interestingly, the same constellation of changes (elevated numbers of low cfos+ cells and decreased number of high c-fos+ cells in CA3 and decreased FFI connectivity) are seen in mice that show impaired contextual memory precision and increased generalization of contextual fear (Ruediger et al., 2011). Furthermore, these observations are reminiscent of elevated CA3 place cell firing in aged rodents (Wilson et al., 2005) and humans (Bakker et al., 2012) during retrieval. Together, these observations suggest that decreased FFI or increased FFE-FFI ratio in aging results in over activation of CA3 during retrieval thereby impeding memory precision and pattern separation-completion balance.

Levels of adult hippocampal neurogenesis are also dramatically reduced with aging (FIG. 1C). Adult-born dg neurons are both necessary and sufficient for pattern separation involving discrimination of similar fearful and safe contexts (Tronel et al., 2010; Sahay et al., 2011; Nakashiba et al., 2012; Niibori et al., 2012) through global remapping in CA3 (Niibori et al., 2012). Interestingly, young adult-born dg neurons exhibit highest number of MFT-filopodia (corresponding to decreased FFE-FFI ratio) at a stage (4 weeks) when they show heightened synaptic plasticity (Snyder et al., 2001; Schmidt-Hieber et al., 2004; Saxe et al., 2006; Ge et al., 2007; Massa et al., 2011) and that there is a progressive reduction in MFT-filopodial number coupled with growth in MFT size, suggestive of decreasing FFI and increasing FFE (corresponding to increasing FFE-FFI ratio), during maturation of adult-born dg neurons (FIG. 4A). One mechanism by which interference between similar inputs is minimized and constrains excessive pattern completion in CA3 is pattern separation through global remapping in CA3, a neural mechanism by which similar environments are encoded by independent or non-overlapping neuronal-ensembles in CA3 (FIG. 1A). Interestingly, adult-born neurons have been shown to be required for global remapping CA3 (Niibori et al., 2012) and aged mice show impaired global remapping in CA3 (Wilson et al., 2005).

To identify molecular regulators of MFT-filopodial plasticity, we performed a screen for targets of a transcription factor, Kruppel-like factor 9 (Klf9), in the DG, which we found to be upregulated as adult-born dg neurons integrate into DG-CA3 circuitry (Scobie et al., 2009). We hypothesized that some Klf9-target genes are likely to play a role in shaping connectivity of adult-born dg neurons. We examined expression patterns of candidate targets by in situ hybridization (ISH) and identified ablim3, a F-Actin binding protein, whose transcripts are highly enriched in dg neurons but not in hilar cell types and are found at low levels in CAL Interestingly, Ablim3 is exclusively localized to MFT-CA3 spine contact sites known as puncta adherens junctions (PAJs) within MFTs, and is absent from other hippocampal molecular layers and elsewhere in adult forebrain (FIG. 3A-C). Because PAJs play a role in structural plasticity and Ablim3 associates with F-actin (Matsuda et al., 2010), we surmised that Ablim3 acts as a brake on MFT structural plasticity with increasing Ablim3 levels stabilizing the MFT and decreasing Ablim3 levels facilitating MFT remodeling and increasing MFT-filopodial number (FIG. 3E). Consistent with this proposal, retroviral overexpression of Ablim3 in adult-born dg neurons increased MFT size (FIG. 4B) and aged mice showed increased levels of Ablim3 expression following training compared with adult mice (FIG. 3D). These data suggest that Ablim3 may be molecularly harnessed to increase FFE connectivity in dg neurons.

Based on these observations and the emerging evidence for FFI in encoding and memory precision (Ruediger et al., 2011; Ruediger et al., 2012), but without wishing to be bound by theory, it was hypothesized that increased FFE (and increased FFE-FFI ratio) causally underlies alterations in CA3 properties and encoding and memory imprecision in aging. Since a lack of young adult-born dg neurons (contributors of high FFI) as well as increased FFE and decreased FFI of mature dg neurons contributes to the increased FFE-FFI ratio in DG-CA3 circuit in aging, we tested whether increasing FFE connectivity by overexpression of Ablim3 in just young adult-born dg neurons in adulthood is sufficient to produce age-related alterations in CA3 properties and encoding and memory imprecision.

Example 1.2. Increasing FFI Connectivity of Mature dg Neurons in Aged Mice is Sufficient to Reverse Aging Related Alterations in CA3 and Encoding and Memory Imprecision We have identified changes in connectivity underlying FFE and FFI in aged mice that we hypothesize causally contributes to hyperactivation of CA3 during retrieval, impaired global remapping in CA3 and impaired discrimination of similar contexts. Specifically, we found that mature dg neurons show increased MFT size, a profound reduction in MFT-filopodial contacts with SL PV+ interneurons and impaired learning induced enhancement in FFI (FIG. 1A-B, FIG. 2E-F). Furthermore, young adult-born dg neurons, which are indispensable for pattern separation (Tronel et al., 2010; Sahay et al., 2011; Nakashiba et al., 2012; Niibori et al., 2012) through global remapping in CA3 (Niibori et al., 2012) exhibit highest FFI connectivity (FIG. 4A). Since aged mice show negligible levels of adult hippocampal neurogenesis (FIG. 1C), reengineering FFI connectivity of mature dg neurons to young adult-born dg neuron-like state may restore E-I and pattern separation-completion balance and reverse CA3 hyperactivation during retrieval.

Based on our model for Ablim3 functions in MFT remodeling during learning (FIG. 3E), we interrogated the impact of selective downregulation of Ablim3 in mature dg neurons in adult (2 months) and aged (16 months) mice.

Figure 5A:
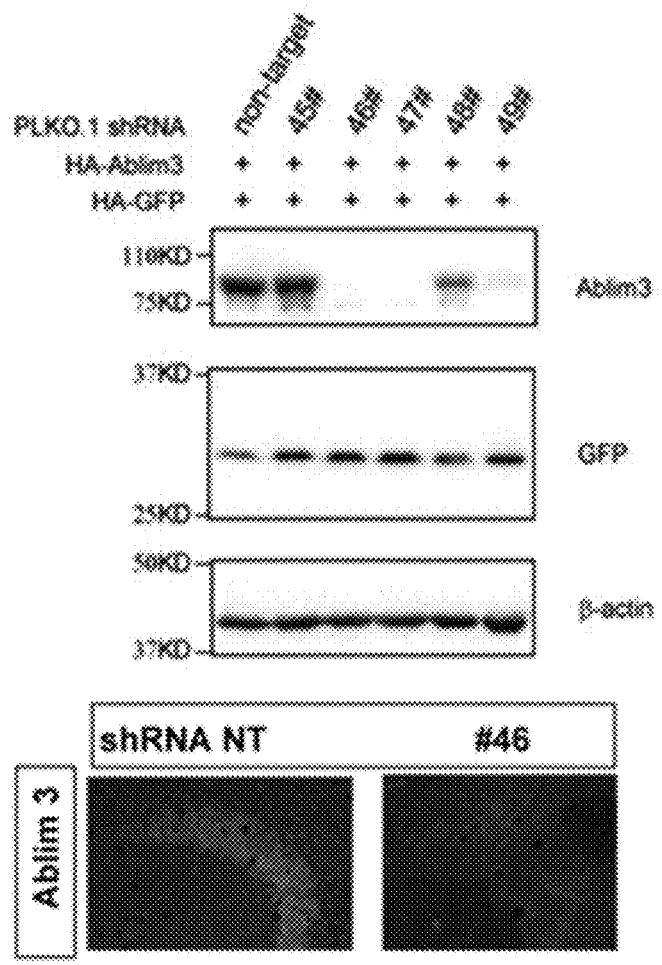
Figure 5B:
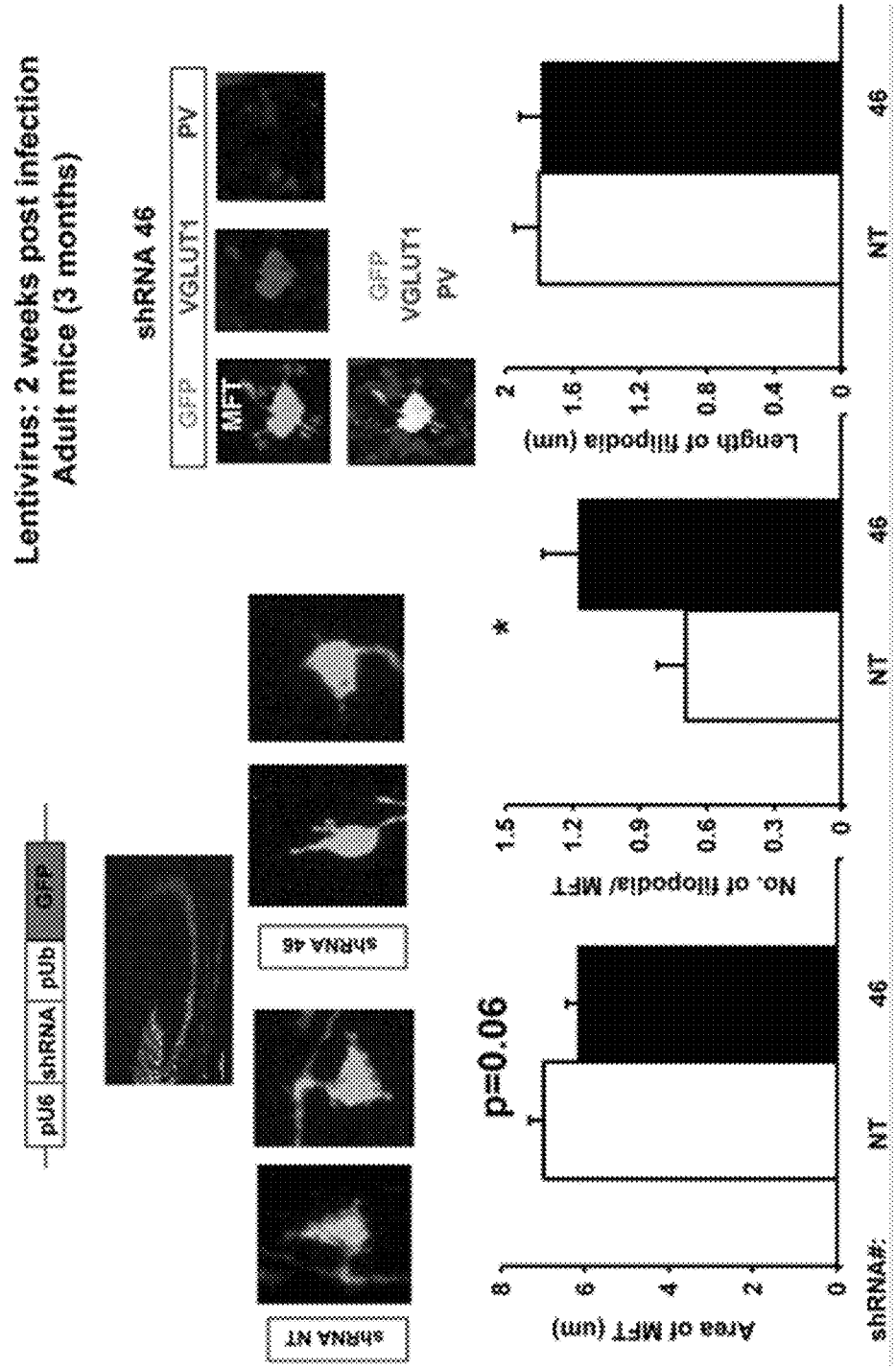
Figure 5D:
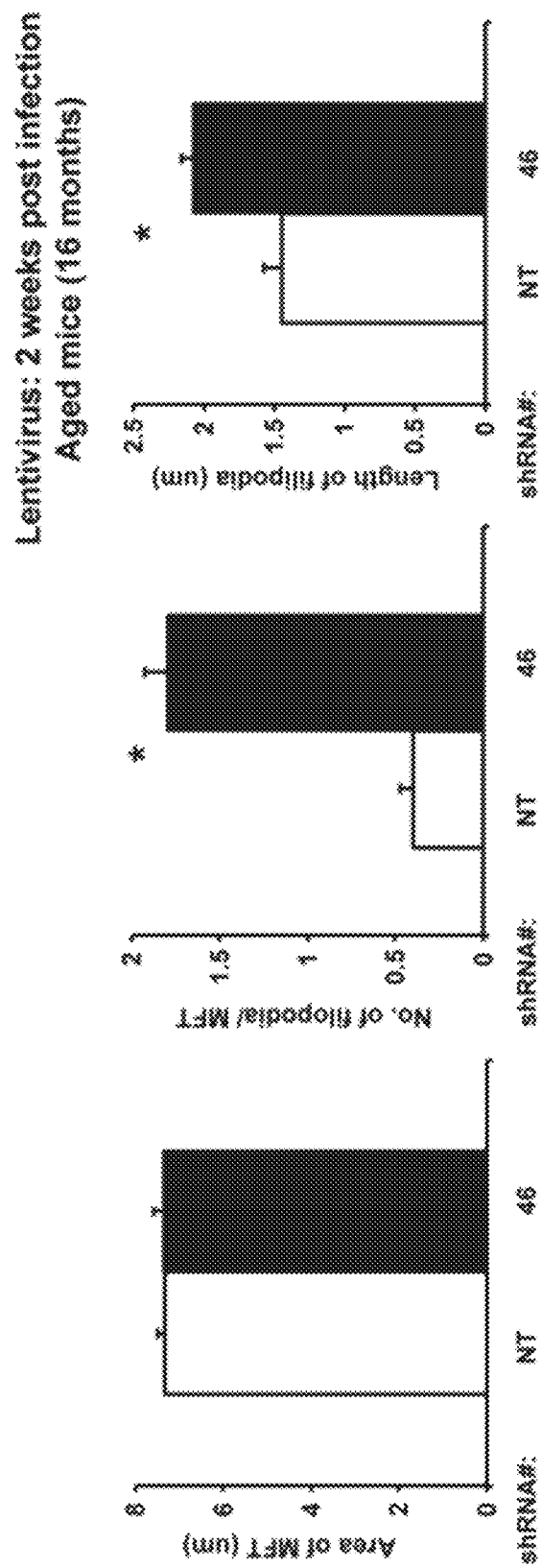

Using lentivirally expressed shRNAs that downregulate Ablim3 levels (FIG. 5A), we found that we can dramatically increase the number of VGLUT1+ MFT-filopodial contacts of mature dg neurons with SL PV+ interneurons in both adult and aged mice without affecting dg neuronal dendritic spine density (FIG. 5B-D). These results suggest that downregulating Ablim3 levels in mature dg neurons of aged mice can reverse aging related alterations in CA3 and encoding and memory imprecision.

Figure 5E:
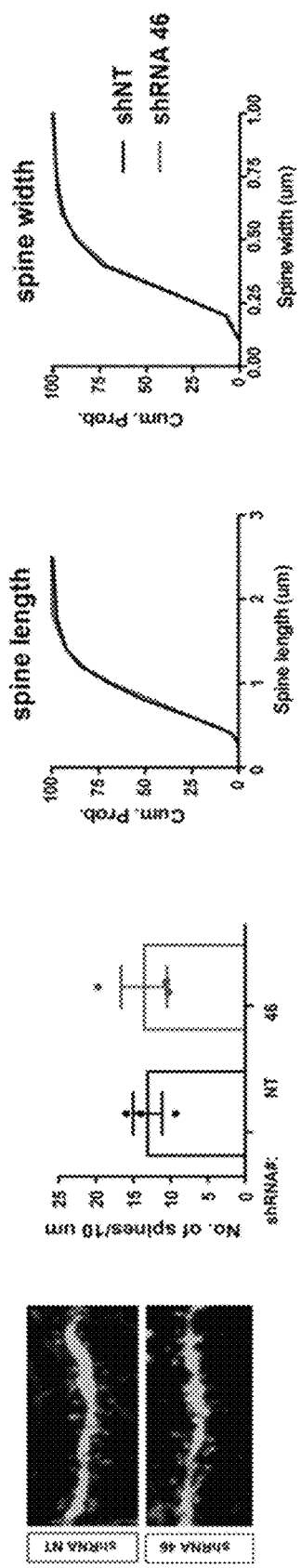
Figure 5F:
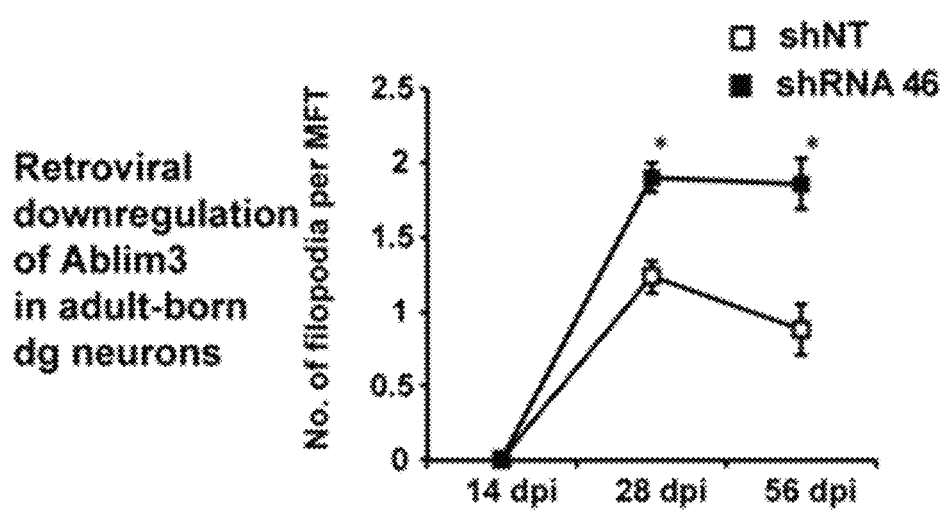

To determine if Ablim3 acts as a brake on MFT filopodial plasticity in mature dg neurons in vivo, we engineered lentiviruses to express GFP and shRNA #46 or a NT shRNA (FIG. 5A-B). We injected viruses expressing these shRNAs into the dorsal DG of adult (3 months old) or aged (16 months old) female C57BL/6 mice and performed confocal microscopy to examine the MFT and MFT-filopodia at 2 weeks p.i. Downregulation of Ablim3 significantly increased the number of VGLUT1+MFT-filopodial contacts with SL PV+ interneurons in CA3ab and did not affect dendritic spine density (FIG. 5B-D). Importantly, Ablim3 downregulation restored the number of VGLUT1+MFT-filopodial contacts of mature dg neurons with SL PV+ interneurons to levels seen in 4 weeks old adult-born dg neurons (FIG. 4A). That two different shRNAs (nos. 46 and 47, data not shown) produced identical phenotypes using lentiviruses argues against the contribution of off-target effects of shRNA to the observed phenotypes. In a separate series of experiments, we used a retroviral expression system to downregulate Ablim3 just in adult-born dg neurons. As is evident in FIG. 5E, downregulation of Ablim3 in adult-born dg neurons produced long-lasting, persistent enhancement in number of MFT-filopodia. Since ablim3 expression is restricted to dg neurons in DG and is absent from mossy cell and hilar interneurons, we expect our manipulation to specifically enhance FFI connectivity of mature dg neurons without changing input specificity or properties of other neuronal cell types in DG.

Example 2. Identifying Small Molecule Negative Regulators of Ablim3 Function Using a Cell-Based Assay for Ablim3 Localization The generation of small molecule regulators of Ablim3 will enable pharmacological modulation of pattern separation in the diseased brain. Without wishing to be bound by theory, it is hypothesized that the localization of ablim3 to the PAJ is critical for its regulation of MF filopodia and synaptic remodeling. Therefore, disrupting ablim3 localization should mimic ablim3 loss of function and increase MF filopodial plasticity.

Heterologous GFP-ablim3 expression in NIH3T3 fibroblasts confines ablim3 to adherens junctions at sites of cell-cell contact (Matsuda et al., 2010). A stable NIH3T3 fibroblasts cell line that over expresses GFP-ablim3 is generated (FIG. 6A). The NINDs custom collection 2 library of characterized bioactive compounds is used to screen for small molecule disruptors of ablim3 localization at adherens junctions. This is done by analyzing GFP-ablim3 at the adherens junctions (light grey crossed lines 'x' in top left panel of FIG. 6B) following processing wells of compound-treated cells with antibodies against GFP and ZO1 (dark grey crossed lines 'x' in top right panel of FIG. 6B). This screen may be made high throughput by automating the quantification. Putative candidates that also disrupt the actin cytoskeleton are eliminated since this will affect ablim3 localization. All compounds are tested in triplicate and at different doses to generate dose response curves.

The function of ablim3 in MF filopodial plasticity and ciliogenesis appears to be remarkably conserved, i.e. down regulation of ablim3 in a ciliated cell line increases the number and length of cilia (Cao et al., 2012). Repression of branched F-actin (necessary for lamellopodia) is thought to facilitate ciliogenesis (Cao et al., 2012) and act downstream to the endocytic recycling pathway (Kim et al., 2010). Since ablim3 represses branched F-actin (hence the smaller MFTs, FIG. 3C (Cao et al., 2012)), whether candidate compounds identified in the localization screen increase cilia length and number without affecting vesicle recycling is ascertained. A ciliated cell line is used in which cilia is genetically labeled with red fluorescent protein, RFP, (Ivs:Tag RFPT) that also expresses GFP tagged Smoothened receptor (GFP-Smo) developed by Andy McMahon, Lee Rubin and colleagues (Wang et al., 2012). The Smo-GFP allows assessment of effects on the endocytic vesicle pathway. An automated screening protocol as done by Lee Rubin and colleagues (Wang et al., 2012) is used to assess changes in cilia length and number and alterations in Smo-GFP localization.

For target validation, shRNAs against ablim3 are used to assess specificity of the small molecule candidates. If disrupting ablim3-PAJ association confers a loss of function phenotype, then small molecule treatment of ciliated cells that express ablim3 shRNA should not augment cilia number or length.

Molecules that disrupt GFP-ablim3 localization to adherens junctions, but not actin stress fibers, are candidates for inhibiting ablim3 in vivo. The cilia screen will further validate candidate molecules.

Example 3. Assess Procognitive Potential of Small Molecule Regulators of Ablim3 in Aged Mice Small molecules that disrupt ablim3 localization to adherens junctions in vitro are likely to inhibit ablim3 localization to PAJs in vivo. Here, without wishing to be bound by theory, it is hypothesized that small molecule inhibitors of ablim3 localization to PAJs will produce the same phenotypes as ablim3 downregulation, i.e. increased filopodia number and length and enhance pattern separation.

The dose necessary to enhance MF filopodia in vivo is determined A candidate small molecule is administered intraperitoneally at different doses to genetic reporter mice (Thy-1 M GFP) that allow us to visualize MF filopodia. Once the dose is established, the behavioral impact of small molecule enhancement of MF filopodia is assessed. In contrast to viral manipulations which are sustained due to viral integration in the genome, small molecules will afford temporal control of MF filopodial plasticity. Since aged mice show impaired pattern separation (Creer et al., 2010), whether pattern separation impairments in aged mice can be reversed is assessed using behavioral paradigms described above.

Example 4. FFE-FFI Balance Mediated by Adult-Born Dg Neurons is Necessary for Pattern Separation of Contexts and Predictors of Contingency by Global Remapping Adult-born dg neurons have been found to be both necessary and sufficient for pattern separation involving discrimination of similar fearful and safe contexts (Tronel et al., 2010; Sahay et al., 2011b; Nakashiba et al., 2012; Niibori et al., 2012) through global remapping in CA3 (Niibori et al., 2012). However, the mechanisms by which adult-born dg neurons contribute to pattern separation are poorly understood. Without wishing to be bound by theory, the present inventors propose a role for E-I balance in mediating the effects of adult-born neurons on pattern separation. Furthermore, it is proposed that adult-born dg neuron dependent pattern separation also underlie discrimination of cues that predict contingency through global remapping in CA3. The basis for this proposal is as follows: 1. The hippocampus has been shown to participate in encoding uncertainty of cue-contingency associations in humans (Vanni-Mercier et al., 2009). 2. Silencing the DG in an "anxious" serotonin mouse mutant ameliorates discrimination of predictors of contingency, whereas impaired discrimination of predictors of contingency is associated with increased activation of the DG (Tsetsenis et al., 2007; Enkel et al., 2010). 3. Sparseness of activation in DG, a property important for pattern separation by global remapping, may be modulated by adult hippocampal neurogenesis (Sahay et al., 2011a; Piatti et al., 2013). 4. Global remapping in DG is seen when different search strategies within the same spatial maze are used suggesting that it may be a general mechanism to minimize interference, independent of modality and spatial cue processing (Satvat et al., 2011). The wiring diagram of the DG-CA3 circuit shows exquisite anatomical segregation of FFE and FFI within the MFT (Acsady et al., 1998; McBain, 2008). Specifically, dg neurons make excitatory connections with CA3 neurons via large MFTs and onto parvalbumin (PV) +ve inhibitory interneurons in stratum lucidum via vesicular glutamate transporter-1 (VGLUT1) +ve filopodia emanating from the MFTs (FIG. 1A). Since these interneurons inhibit CA3 neurons, the synaptic connections of MFT filopodia and MFTs influence excitation-inhibition balance, a property thought to be important for sparse encoding in the DG-CA3 circuit (O'Reilly and McClelland, 1994; Rolls, 1996; Mori et al., 2007; Treves et al., 2008; Ferrante et al., 2009; Ruediger et al., 2011; Ruediger et al., 2012; Piatti et al., 2013). Moreover, MFT filopodia exhibit plasticity in response to learning and MFT filopodia number correlate very tightly with memory precision (Ruediger et al., 2011; Ruediger et al., 2012).

Figure 7A:
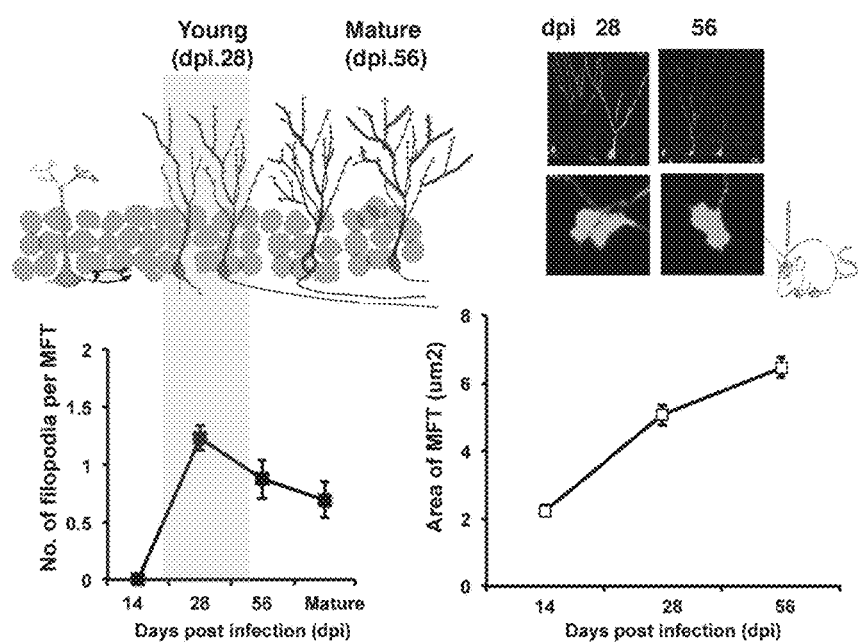
FIGS. 7A-B. MFT Filopodia number and MFT size during dg neuronal maturation and following a context discrimination-pattern separation task. 7A. 4 wk adult-born neurons show highest MFT filopodia number but MFT size increases with maturation. Inset: Retroviral labeled adult-born dg neurons and MFTs. 7B. MFT Filopodia number increases following discrimination between shock context A and similar context B (Freezing in A>B). At least n=50 MFTs (B-C) and n=3 mice per timepoint (B). n=12 mice (C). Data are mean+/−S.E.M. *p<0.05.

Green fluorescent protein (GFP)-expressing retroviruses were used to genetically label adult-born dg neurons at distinct stages of maturation (14, 28 and 56 dpi) in C57BL/6J mice and MFT size and MFT filopodia were analyzed by confocal microscopy (FIG. 1A, 7A). Mature dg neurons were infected with lentivirus expressing GFP and two weeks later MFT filopodia were analyzed following a contextual fear discrimination task previously shown to require pattern separation and global remapping in CA3 (Sahay et al., 2011b; Nakashiba et al., 2012; Niibori et al., 2012; Deng et al., 2013)(FIG. 7B) as follows. Briefly, mice had to distinguish a context in which they received a foot shock (context A) from a similar safe context "B". The mice were also tested in a completely different context "C" to ascertain if an observed discrimination phenotype is restricted to conditions with high context similarity indicative of a pattern separation-impairment and not another encoding function (Niibori et al., 2012; Deng et al., 2013). Mice were analyzed on day 3 following exposure to just context B.

Figure 7B:
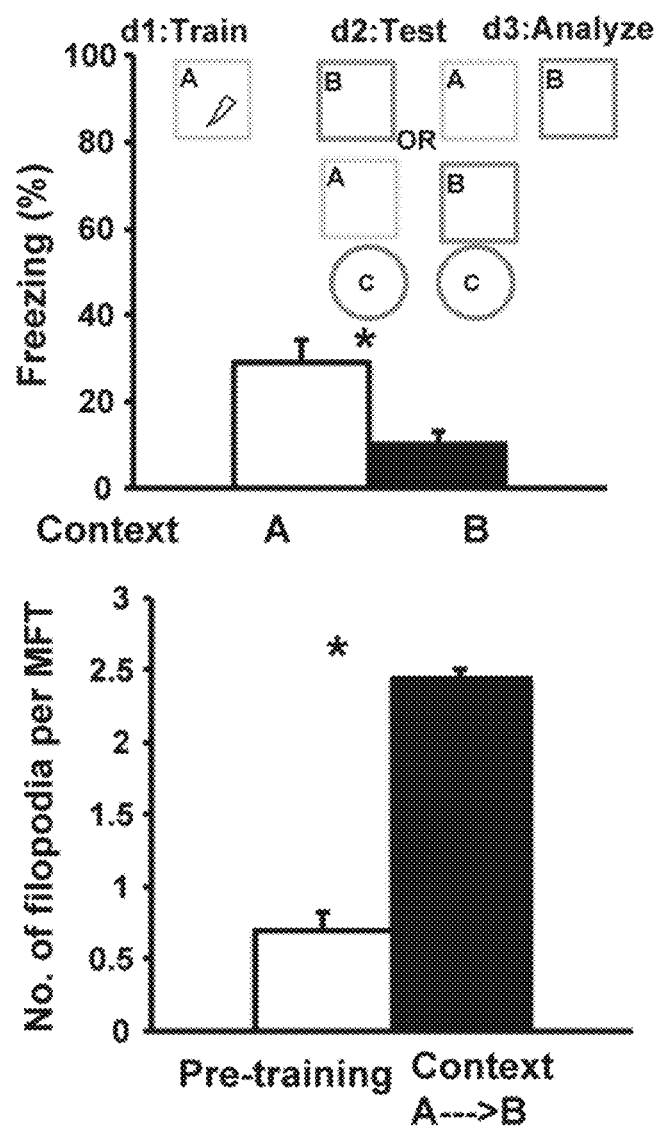

We found that adult-born dg neurons exhibit highest number of MFT filopodia (decreased FFE-FFI ratio) at a stage (4 weeks) when they show heightened synaptic plasticity (Snyder et al., 2001; Schmidt-Hieber et al., 2004; Saxe et al., 2006; Ge et al., 2007; Massa et al., 2011) and that there is a progressive restriction in filopodial number coupled with growth in MFT size, suggestive of decreasing FFI and increasing FFE (increasing FFE-FFI ratio), during maturation of adult-born dg neurons (FIG. 7A). Furthermore, MFT filopodia number in mature dg neurons is increased following discrimination of similar contexts, a task thought to require pattern separation (Sahay et al., 2011b; Nakashiba et al., 2012; Niibori et al., 2012; Deng et al., 2013) (FIG. 7B). Thus, modulation of MFT filopodial plasticity and MFT size of adult-born neurons may dictate FFI-FFE balance in DG-CA3 and consequently, pattern separation.

As described above, Ablim3 was identified in a screen for targets of Klf9; Ablim3 is exclusively localized to MFT-CA3 spine contact sites known as puncta adherens junctions (PAJs) within MFTs, and is absent from other hippocampal molecular layers and elsewhere in adult forebrain. The localization of Ablim3 suggests that it may act as a brake on structural plasticity and its downregulation facilitates synapse remodeling and MFT plasticity (FIG. 3A-D). Retroviral regulation of Ablim3 levels in adult-born neurons (FIG. 4) diametrically regulates FFE and FFI and since small MFTs that innervate hilar interneurons do not have PAJs, Ablim3 may be harnessed to selectively modulate FFE-FFI balance (without affecting feedback inhibition onto the DG) in adult-born neurons.

Figure 8A:
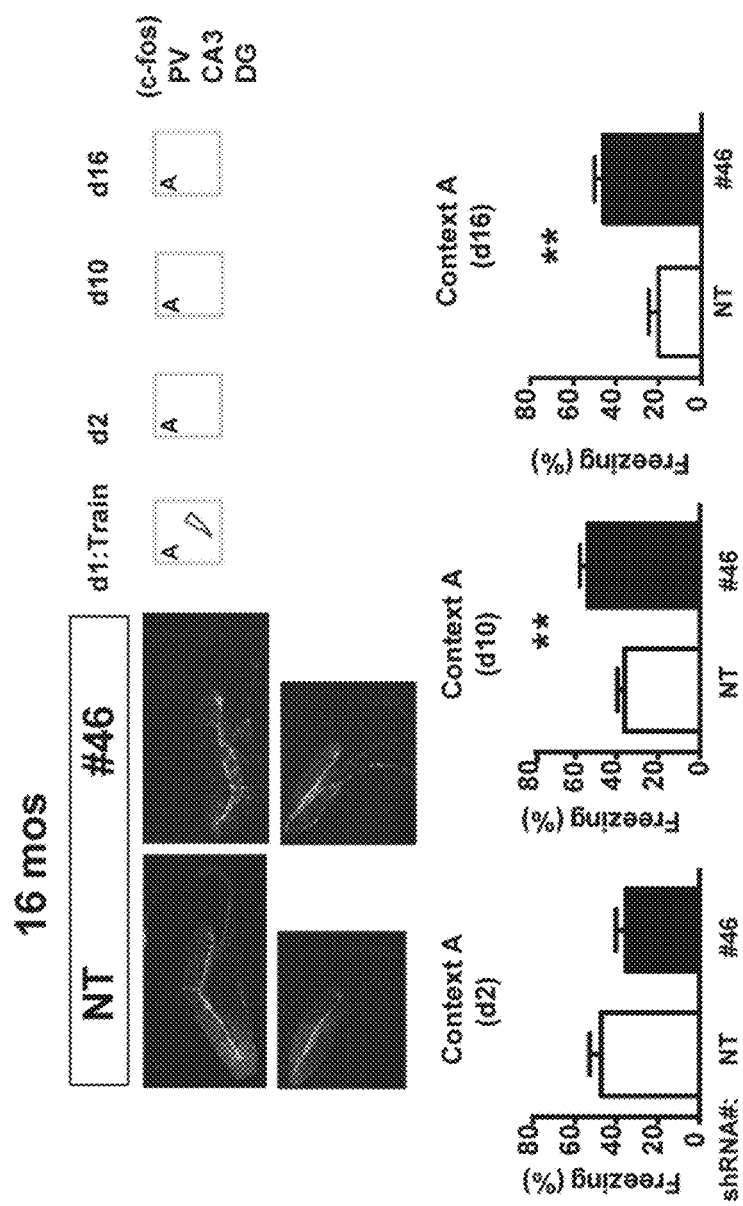

Furthermore, Ablim3 down regulation in dg neurons of aged mice was sufficient to enhance long-term contextual fear memory, activation of PV interneurons, number of c-fos (high) in CA3 neurons without affecting DG activation. Downregulation of Ablim3 using virally-administered shRNA causally increased PV+ activation, number of c-fos (high) cells in CA3 and long-term contextual fear memory. Consistent with Ablim3 absent in mossy cell and hilar interneurons, DG activation was unchanged and feed-back inhibition was maintained (FIGS. 8A-C).

REFERENCES

Acsady L, Kali S (2007) Models, structure, function: the transformation of cortical signals in the dentate gyrus. Prog Brain Res 163:577-599.
Acsady L, Kamondi A, Sik A, Freund T, Buzsaki G (1998) GABAergic cells are the major postsynaptic targets of mossy fibers in the rat hippocampus. J Neurosci 18:3386-3403.
Bakker A, Kirwan C B, Miller M, Stark C E (2008) Pattern separation in the human hippocampal CA3 and dentate gyrus. Science 319:1640-1642.
Bakker A, Krauss G L, Albert M S, Speck C L, Jones L R, Stark C E, Yassa M A, Bassett S S, Shelton A L, Gallagher M (2012) Reduction of hippocampal hyperactivity improves cognition in amnestic mild cognitive impairment. Neuron 74:467-474.
Barnes C A, McNaughton B L (1980) Physiological compensation for loss of afferent synapses in rat hippocampal granule cells during senescence. The Journal of physiology 309:473-485.
Biedenkapp J C, Rudy J W (2007) Context preexposure prevents forgetting of a contextual fear memory: implication for regional changes in brain activation patterns associated with recent and remote memory tests. Learning & memory (Cold Spring Harbor, N.Y. 14:200-203.
Blanchard R J, Hebert M A, Ferrari P F, Palanza P, Figueira R, Blanchard D C, Parmigiani S (1998) Defensive behaviors in wild and laboratory (Swiss) mice: the mouse defense test battery. Physiol Behav 65:201-209.
Boldrini M, Hen R, Underwood M D, Rosoklija G B, Dwork A J, Mann J J, Arango V (2012) Hippocampal angiogenesis and progenitor cell proliferation are increased with antidepressant use in major depression. Biol Psychiatry 72:562-571.
Boldrini M, Underwood M D, Hen R, Rosoklija G B, Dwork A J, John Mann J, Arango V (2009) Antidepressants increase neural progenitor cells in the human hippocampus. Neuropsychopharmacology 34:2376-2389.
Bragin A, Jando G, Nadasdy Z, van Landeghem M, Buzsaki G (1995) Dentate EEG spikes and associated interneuronal population bursts in the hippocampal hilar region of the rat. J Neurophysiol 73:1691-1705.
Campeau S, Watson S J, Jr. (2000) Connections of some auditory-responsive posterior thalamic nuclei putatively involved in activation of the hypothalamo-pituitary-adrenocortical axis in response to audiogenic stress in rats: an anterograde and retrograde tract tracing study combined with Fos expression. J Comp Neurol 423:474-491.
Cao J, Shen Y, Zhu L, Xu Y, Zhou Y, Wu Z, Li Y, Yan X, Zhu X (2012) miR-129-3p controls cilia assembly by regulating CP110 and actin dynamics. Nature cell biology 14:697-706.

Clelland C D, Choi M, Romberg C, Clemenson G D, Jr., Fragniere A, Tyers P, Jessberger S, Saksida L M, Barker R A, Gage F H, Bussey T J (2009) A functional role for adult hippocampal neurogenesis in spatial pattern separation. Science 325:210-213.

Couillard-Despres S, Winner B, Schaubeck S, Aigner R, Vroemen M, Weidner N, Bogdahn U, Winkler J, Kuhn H G, Aigner L (2005) Doublecortin expression levels in adult brain reflect neurogenesis. Eur J Neurosci 21:1-14.

Creer D J, Romberg C, Saksida L M, van Praag H, Bussey T J (2010) Running enhances spatial pattern separation in mice. Proc Natl Acad Sci USA 107:2367-2372.

Crestani F, Lorez M, Baer K, Essrich C, Benke D, Laurent J P, Belzung C, Fritschy J M, Luscher B, Mohler H (1999) Decreased GABAA-receptor clustering results in enhanced anxiety and a bias for threat cues. Nat Neurosci 2:833-839.

Decker M W (1987) The effects of aging on hippocampal and cortical projections of the forebrain cholinergic system. Brain Res 434:423-438.

Deng W, Mayford M, Gage F H (2013) Selection of distinct populations of dentate granule cells in response to inputs as a mechanism for pattern separation in mice. eLife 2:e00312.

Enkel T, Gholizadeh D, von Bohlen Und Halbach O, Sanchis-Segura C, Hurlemann R, Spanagel R, Gass P, Vollmayr B (2010) Ambiguous-cue interpretation is biased under stress- and depression-like states in rats. Neuropsychopharmacology 35:1008-1015.

Ferrante M, Migliore M, Ascoli G A (2009) Feed-forward inhibition as a buffer of the neuronal input-output relation. Proc Natl Acad Sci USA 106:18004-18009.

Frankland P W, Cestari V, Filipkowski R K, McDonald R J, Silva A J (1998) The dorsal hippocampus is essential for context discrimination but not for contextual conditioning. Behav Neurosci 112:863-874.

Ge S, Yang C H, Hsu K S, Ming G L, Song H (2007) A critical period for enhanced synaptic plasticity in newly generated neurons of the adult brain. Neuron 54:559-566.

Geinisman Y, deToledo-Morrell L, Morrell F, Persina I S, Rossi M (1992) Age-related loss of axospinous synapses formed by two afferent systems in the rat dentate gyrus as revealed by the unbiased stereological dissector technique. Hippocampus 2:437-444.

Gilbert P E, Kesner R P, Lee I (2001) Dissociating hippocampal subregions: double dissociation between dentate gyrus and CA1. Hippocampus 11:626-636.

Grillon C, Pine D S, Lissek S, Rabin S, Bonne O, Vythilingam M (2009) Increased anxiety during anticipation of unpredictable aversive stimuli in posttraumatic stress disorder but not in generalized anxiety disorder. Biol Psychiatry 66:47-53.

Gu Y, Arruda-Carvalho M, Wang J, Janoschka S R, Josselyn S A, Frankland P W, Ge S (2012) Optical controlling reveals time-dependent roles for adult-born dentate granule cells. Nat Neurosci 15:1700-1706.

Guzowski J F, McNaughton B L, Barnes C A, Worley P F (1999) Environment-specific expression of the immediate-early gene Arc in hippocampal neuronal ensembles. Nat Neurosci 2:1120-1124.

Hasselmo M E, Schnell E, Barkai E (1995) Dynamics of learning and recall at excitatory recurrent synapses and cholinergic modulation in rat hippocampal region CA3. J Neurosci 15:5249-5262.

Hof P R, Morrison J H (2004) The aging brain: morphomolecular senescence of cortical circuits. Trends Neurosci 27:607-613.

Ikrar T, Guo N, He K, Besnard A, Levinson S, Hill A, Lee H-K, Hen R, Xu X, Sahay A (2013) Adult neurogenesis modifies excitability of the dentate gyrus. Front Neural Circuits 7: 204.

Jovanovic T, Ressler K J (2010) How the neurocircuitry and genetics of fear inhibition may inform our understanding of PTSD. Am J Psychiatry 167:648-662.

Kheirbek M A, Klemenhagen K C, Sahay A, Hen R (2012) Neurogenesis and generalization: a new approach to stratify and treat anxiety disorders. Nature Neuroscience 15.

Kim J, Lee J E, Heynen-Genel S, Suyama E, Ono K, Lee K, Ideker T, Aza-Blanc P, Gleeson J G (2010) Functional genomic screen for modulators of ciliogenesis and cilium length. Nature 464:1048-1051.

Knoth R, Singec I, Ditter M, Pantazis G, Capetian P, Meyer R P, Horvat V, Volk B, Kempermann G (2010) Murine features of neurogenesis in the human hippocampus across the lifespan from 0 to 100 years. PLoS ONE 5:e8809.

Krause M, Yang Z, Rao G, Houston F P, Barnes C A (2008) Altered dendritic integration in hippocampal granule cells of spatial learning-impaired aged rats. J Neurophysiol 99:2769-2778.

Kubik S, Miyashita T, Guzowski J F (2007) Using immediate-early genes to map hippocampal subregional functions. Learning & memory (Cold Spring Harbor, N.Y. 14:758-770.

Kuhn H G, Dickinson-Anson H, Gage F H (1996) Neurogenesis in the dentate gyrus of the adult rat: age-related decrease of neuronal progenitor proliferation. J Neurosci 16:2027-2033.

Leutgeb J K, Leutgeb S, Moser M B, Moser E I (2007) Pattern separation in the dentate gyrus and CA3 of the hippocampus. Science 315:961-966.

Lin D, Boyle M P, Dollar P, Lee H, Lein E S, Perona P, Anderson D J (2011) Functional identification of an aggression locus in the mouse hypothalamus. Nature 470:221-226.

Lissek S, Rabin S, Heller R E, Lukenbaugh D, Geraci M, Pine D S, Grillon C (2010) Overgeneralization of conditioned fear as a pathogenic marker of panic disorder. Am J Psychiatry 167:47-55.

Marr D (1971) Simple memory: a theory for archicortex. Philosophical transactions of the Royal Society of London 262:23-81.

Massa F, Koelh M, Wiesner T, Grosjean N, Revest J M, Piazza P V, Abrous D N, Oliet S H (2011) Conditional reduction of adult neurogenesis impairs bidirectional hippocampal synaptic plasticity. Proc Natl Acad Sci USA 108:6644-6649.

Matsuda M, Yamashita J K, Tsukita S, Furuse M (2010) abLIM3 is a novel component of adherens junctions with actin-binding activity. European journal of cell biology 89:807-816.

McBain C J (2008) Differential mechanisms of transmission and plasticity at mossy fiber synapses. Prog Brain Res 169:225-240.

McClelland J L, Goddard N H (1996) Considerations arising from a complementary learning systems perspective on hippocampus and neocortex. Hippocampus 6:654-665.

McHugh T J, Jones M W, Quinn J J, Balthasar N, Coppari R, Elmquist J K, Lowell B B, Fanselow M S, Wilson M A, Tonegawa S (2007) Dentate Gyrus NMDA Receptors Mediate Rapid Pattern Separation in the Hippocampal Network. Science 317:94-99.

McNaughton B, Morris R (1987) Hippocampal synaptic enhancement and information storage within a distributed memory system. Trends Neurosci 10:408-415.

Monosov I E, Hikosaka O (2013) Selective and graded coding of reward uncertainty by neurons in the primate anterodorsal septal region. Nat Neurosci 16:756-762.

Mori M, Gahwiler B H, Gerber U (2007) Recruitment of an inhibitory hippocampal network after bursting in a single granule cell. Proc Natl Acad Sci USA 104:7640-7645.

Motley S E, Kirwan C B (2012) A parametric investigation of pattern separation processes in the medial temporal lobe. J Neurosci 32:13076-13085.

Nakashiba T, Cushman J D, Pelkey K A, Renaudineau S, Buhl D L, McHugh T J, Rodriguez Barrera V, Chittajallu R, Iwamoto K S, McBain C J, Fanselow M S, Tonegawa S (2012) Young dentate granule cells mediate pattern separation, whereas old granule cells facilitate pattern completion. Cell 149:188-201.

Nakazawa K, Quirk M C, Chitwood R A, Watanabe M, Yeckel M F, Sun L D, Kato A, Carr C A, Johnston D, Wilson M A, Tonegawa S (2002) Requirement for hippocampal CA3 NMDA receptors in associative memory recall. Science 297:211-218.

Niibori Y, Yu T S, Epp J R, Akers K G, Josselyn S A, Frankland P W (2012) Suppression of adult neurogenesis impairs population coding of similar contexts in hippocampal CA3 region. Nature communications 3:1253.

Opendak M, Gould E (2011) New neurons maintain efficient stress recovery. Cell Stem Cell 9:287-288.

O'Reilly R C, McClelland J L (1994) Hippocampal conjunctive encoding, storage, and recall: avoiding a trade-off Hippocampus 4:661-682.

Pan W X, McNaughton N (2004) The supramammillary area: its organization, functions and relationship to the hippocampus. Prog Neurobiol 74:127-166.

Peri T, Ben-Shakhar G, Orr S P, Shalev A Y (2000) Psychophysiologic assessment of aversive conditioning in posttraumatic stress disorder. Biol Psychiatry 47:512-519.

Piatti V C, Ewell L A, Leutgeb J K (2013) Neurogenesis in the dentate gyrus: carrying the message or dictating the tone. Front Neurosci 7:50.

Risold P Y, Swanson L W (1996) Structural evidence for functional domains in the rat hippocampus. Science 272:1484-1486.

Risold P Y, Swanson L W (1997) Connections of the rat lateral septal complex. Brain Res Brain Res Rev 24:115-195.

Rolls E T (1996) A theory of hippocampal function in memory. Hippocampus 6:601-620.

Rolls E T, Kesner R P (2006) A computational theory of hippocampal function, and empirical tests of the theory. Prog Neurobiol 79:1-48.

Ruediger S, Spirig D, Donato F, Caroni P (2012) Goal-oriented searching mediated by ventral hippocampus early in trial-and-error learning. Nat Neurosci. Ruediger S, Vittori C, Bednarek E, Genoud C, Strata P, Sacchetti B, Caroni P (2011) Learning-related feedforward inhibitory connectivity growth required for memory precision. Nature 473:514-518.

Sahay A, Scobie K N, Hill A S, O'Carroll C M, Kheirbek M A, Burghardt N S, Fenton A A, Dranovsky A, Hen R (2011) Increasing adult hippocampal neurogenesis is sufficient to improve pattern separation. Nature 472:466-470.

Sahay A, Wilson D A, Hen R (2011a) Pattern separation: a common function for new neurons in hippocampus and olfactory bulb. Neuron 70:582-588.

Satvat E, Schmidt B, Argraves M, Marrone D F, Markus E J (2011) Changes in task demands alter the pattern of zif268 expression in the dentate gyrus. J Neurosci 31:7163-7167.

Sauerhofer E, Pamplona F A, Bedenk B, Moll G H, Dawirs R R, von Horsten S, Wotjak C T, Golub Y (2012) Generalization of contextual fear depends on associative rather than non-associative memory components. Behav Brain Res 233:483-493.

Saxe M D, Battaglia F, Wang J W, Malleret G, David D J, Monckton J E, Garcia A D, Sofroniew M V, Kandel E R, Santarelli L, Hen R, Drew M R (2006) Ablation of hippocampal neurogenesis impairs contextual fear conditioning and synaptic plasticity in the dentate gyrus. Proc Natl Acad Sci USA 103:17501-17506.

Schmidt B, Marrone D F, Markus E J (2012) Disambiguating the similar: the dentate gyrus and pattern separation. Behav Brain Res 226:56-65.

Schmidt-Hieber C, Jonas P, Bischofberger J (2004) Enhanced synaptic plasticity in newly generated granule cells of the adult hippocampus. Nature 429:184-187.

Scobie K N, Hall B J, Wilke S A, Klemenhagen K C, Fujii-Kuriyama Y, Ghosh A, Hen R, Sahay A (2009) Kruppel-like factor 9 is necessary for late-phase neuronal maturation in the developing dentate gyrus and during adult hippocampal neurogenesis. J Neurosci 29:9875-9887.

Small S A, Chawla M K, Buonocore M, Rapp P R, Barnes C A (2004) Imaging correlates of brain function in monkeys and rats isolates a hippocampal subregion differentially vulnerable to aging. Proc Natl Acad Sci USA 101:7181-7186.

Small S A, Schobel S A, Buxton R B, Witter M P, Barnes C A (2011) A pathophysiological framework of hippocampal dysfunction in ageing and disease. Nat Rev Neurosci 12:585-601.

Smith M L, Deadwyler S A, Booze R M (1993) 3-D reconstruction of the cholinergic basal forebrain system in young and aged rats. Neurobiol Aging 14:389-392.

Smith T D, Adams M M, Gallagher M, Morrison J H, Rapp P R (2000) Circuit-specific alterations in hippocampal synaptophysin immunoreactivity predict spatial learning impairment in aged rats. J Neurosci 20:6587-6593.

Snyder J S, Kee N, Wojtowicz J M (2001) Effects of adult neurogenesis on synaptic plasticity in the rat dentate gyrus. J Neurophysiol 85:2423-2431.

Spalding K L, Bergmann O, Alkass K, Bernard S, Salehpour M, Huttner H B, Bostrom E, Westerlund I, Vial C, Buchholz B A, Possnert G, Mash D C, Druid H, Frisen J (2013) Dynamics of hippocampal neurogenesis in adult humans. Cell 153:1219-1227.

Stanley D P, Shetty A K (2004) Aging in the rat hippocampus is associated with widespread reductions in the number of glutamate decarboxylase-67 positive interneurons but not interneuron degeneration. J Neurochem 89:204-216.

Stark S M, Yassa M A, Lacy J W, Stark C E (2013) A task to assess behavioral pattern separation (BPS) in humans: Data from healthy aging and mild cognitive impairment. Neuropsychologia.

Thomas E, Dewolfe M, Sancar F, Todi N, Yadin E (2012) Electrophysiological analysis of the interaction between the lateral septum and the central nucleus of the amygdala. Neurosci Lett 524:79-83.

Toner C K, Pirogovsky E, Kirwan C B, Gilbert P E (2009) Visual object pattern separation deficits in nondemented older adults. Learning & memory (Cold Spring Harbor, N.Y. 16:338-342.

Torborg C L, Nakashiba T, Tonegawa S, McBain C J (2010) Control of CA3 output by feedforward inhibition despite developmental changes in the excitation-inhibition balance. J Neurosci 30:15628-15637.

Treves A, Rolls E T (1992) Computational constraints suggest the need for two distinct input systems to the hippocampal CA3 network. Hippocampus 2:189-199.

Treves A, Tashiro A, Witter M E, Moser E I (2008) What is the mammalian dentate gyrus good for? Neuroscience 154:1155-1172.

Tronel S, Belnoue L, Grosjean N, Revest J M, Piazza P V, Koehl M, Abrous D N (2010) Adult-born neurons are necessary for extended contextual discrimination. Hippocampus.

Tsetsenis T, Ma X H, Lo Iacono L, Beck S G, Gross C (2007) Suppression of conditioning to ambiguous cues by pharmacogenetic inhibition of the dentate gyrus. Nat Neurosci 10:896-902.

Vanni-Mercier G, Mauguiere F, Isnard J, Dreher J C (2009) The hippocampus codes the uncertainty of cue-outcome associations: an intracranial electrophysiological study in humans. J Neurosci 29:5287-5294.

Vazdarjanova A, Guzowski J F (2004) Differences in hippocampal neuronal population responses to modifications of an environmental context: evidence for distinct, yet complementary, functions of CA3 and CA1 ensembles. J Neurosci 24:6489-6496.

Villeda S A et al. (2011) The ageing systemic milieu negatively regulates neurogenesis and cognitive function. Nature 477:90-94.

von Bohlen and Halbach O, Zacher C, Gass P, Unsicker K (2006) Age-related alterations in hippocampal spines and deficiencies in spatial memory in mice. Journal of neuroscience research 83:525-531.

Wang S H, Teixeira C M, Wheeler A L, Frankland P W (2009) The precision of remote context memories does not require the hippocampus. Nat Neurosci 12:253-255.

Wang Y, Arvanites A C, Davidow L, Blanchard J, Lam K, Yoo J W, Coy S, Rubin L L, McMahon A P (2012) Selective identification of hedgehog pathway antagonists by direct analysis of smoothened ciliary translo cation. ACS chemical biology 7:1040-1048.

Yang Z, Krause M, Rao G, McNaughton B L, Barnes C A (2008) Synaptic commitment: developmentally regulated reciprocal changes in hippocampal granule cell NMDA and AMPA receptors over the lifespan. J Neurophysiol 99:2760-2768.

Yassa M A, Lacy J W, Stark S M, Albert M S, Gallagher M, Stark C E (2011b) Pattern separation deficits associated with increased hippocampal CA3 and dentate gyrus activity in nondemented older adults. Hippocampus 21:968-979.

Yassa M A, Mattfeld A T, Stark S M, Stark C E (2011a) Age-related memory deficits linked to circuit-specific disruptions in the hippocampus. Proc Natl Acad Sci USA 108:8873-8878.

Yassa M A, Muftuler L T, Stark C E (2010) Ultrahigh-resolution microstructural diffusion tensor imaging reveals perforant path degradation in aged humans in vivo. Proc Natl Acad Sci USA 107:12687-12691.

Yassa M A, Stark C E (2011) Pattern separation in the hippocampus. Trends Neurosci 34:515-525.

Yehuda R, LeDoux J (2007) Response variation following trauma: a translational neuroscience approach to understanding PTSD. Neuron 56:19-32.

Zhang J H, Chung T D, Oldenburg K R (1999) A Simple Statistical Parameter for Use in Evaluation and Validation of High Throughput Screening Assays. Journal of biomolecular screening 4:67-73.

Zhou Z, Hong E J, Cohen S, Zhao W N, Ho H Y, Schmidt L, Chen W G, Lin Y, Savner E, Griffith E C, Hu L, Steen J A, Weitz C J, Greenberg M E (2006) Brain-specific phosphorylation of MeCP2 regulates activity-dependent Bdnf transcription, dendritic growth, and spine maturation. Neuron 52:255-269.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: sequence encoding short hairpin RNA

<400> SEQUENCE: 1
aaacccaggg ctgccttgga aaag                                            24
```

Wilson I A, Ikonen S, Gallagher M, Eichenbaum H, Tanila H (2005) Age-associated alterations of hippocampal place cells are subregion specific. J Neurosci 25:6877-6886.

Wiltgen B J, Silva A J (2007) Memory for context becomes less specific with time. Learning & memory (Cold Spring Harbor, N.Y. 14:313-317.

Xu W, Sudhof T C (2013) A neural circuit for memory specificity and generalization. Science 339:1290-1295.

What is claimed is:

1. A method of improving memory in a subject, the method comprising:
   identifying a subject who is in need of improved memory; and
   administering to the subject an effective amount of an inhibitory nucleic acid targeting actin binding LIM protein family, member 3 (ABLIM3).

2. The method of claim 1, wherein the subject has memory dysfunction associated with normal aging or Alzheimer's Disease.

3. The method of claim 1, wherein the subject has post-traumatic stress disorder.

4. The method of claim 1, wherein pattern separation is improved in the subject.

5. The method of claim 1, wherein the inhibitory nucleic acid is 5 to 50 bases in length.

6. The method of claim 1, wherein the inhibitory nucleic acid comprises a base sequence at least 90% complementary to at least 10 bases of the Ablim3 RNA sequence.

7. The method of claim 1, wherein the inhibitory nucleic acid is single stranded.

8. The method of claim 1, wherein the inhibitory nucleic acid is double stranded.

9. The method of claim 1, wherein the inhibitory nucleic acid comprises one or more modifications comprising: a modified sugar moiety, a modified internucleoside linkage, a modified nucleotide, or combinations thereof.

10. The method of claim 1, wherein the inhibitory nucleic acid is an antisense oligonucleotide, LNA, PNA, external guide sequence (EGS) oligonucleotide, or single- or double-stranded RNA interference (RNAi) compound.

11. The method of claim 8, wherein the inhibitory nucleic acid comprises an overhang at one or both termini.

12. The method of claim 9, wherein the modified internucleoside linkage comprises at least one of: alkylphosphonate, phosphorothioate, phosphorodithioate, alkylphosphonothioate, phosphoramidate, carbamate, carbonate, phosphate triester, acetamidate, carboxymethyl ester, or combinations thereof.

13. The method of claim 9, wherein the modified sugar moiety comprises a 2'-O-methoxyethyl modified sugar moiety, a 2'-methoxy modified sugar moiety, a 2'-O-alkyl modified sugar moiety, or a bicyclic sugar moiety.

14. The method of claim 1, wherein the inhibitory nucleic acid comprises one or more modifications selected from the group including 2'-OMe, 2'-F, LNA, PNA, FANA, ENA or morpholino modifications.

15. The method of claim 10, wherein the antisense oligonucleotide is selected from the group consisting of antisense RNAs, antisense DNAs, and chimeric antisense oligonucleotides.

\* \* \* \* \*

UNITED STATES PATENT AND TRADEMARK OFFICE
CERTIFICATE OF CORRECTION

PATENT NO.          : 10,287,580 B2
APPLICATION NO.     : 15/125796
DATED               : May 14, 2019
INVENTOR(S)         : Amar Sahay and Nannan Guo It is certified that error appears in the above-identified patent and that said Letters Patent is hereby corrected as shown below:

In the Specification

Column 1, Line 13, insert -- STATEMENT OF FEDERALLY SPONSORED RESEARCH
This invention was made with government support under Grant Nos. MH104175, and AG048908 awarded by the National Institutes of Health. The government has certain rights in the invention. --

Signed and Sealed this
Twenty-third Day of May, 2023

Katherine Kelly Vidal
*Director of the United States Patent and Trademark Office*